(12) United States Patent
Swager et al.

(10) Patent No.: US 8,802,447 B2
(45) Date of Patent: Aug. 12, 2014

(54) EMISSIVE COMPOSITIONS WITH INTERNAL STANDARD AND RELATED TECHNIQUES

(75) Inventors: Timothy M. Swager, Newton, MA (US); Jessica H. Liao, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 502 days.

(21) Appl. No.: 11/595,833

(22) Filed: Nov. 10, 2006

(65) Prior Publication Data

US 2008/0085566 A1     Apr. 10, 2008

Related U.S. Application Data

(60) Provisional application No. 60/849,547, filed on Oct. 5, 2006.

(51) Int. Cl.
*G01N 33/544* (2006.01)
*G01N 33/551* (2006.01)
*G01N 33/553* (2006.01)
*G01N 33/24* (2006.01)
*C09K 11/57* (2006.01)
*C09K 11/06* (2006.01)
*G01N 33/545* (2006.01)

(52) U.S. Cl.
CPC ............ *G01N 33/544* (2013.01); *G01N 33/553* (2013.01); *C09K 11/574* (2013.01); *C09K 11/06* (2013.01); *G01N 33/545* (2013.01); *C09K 2211/1416* (2013.01)
USPC ........... 436/528; 436/524; 436/525; 436/531; 436/81; 436/172

(58) Field of Classification Search
CPC ................. C09K 11/574; C09K 11/06; C09K 2211/1416; G01N 33/545; H01L 51/502
See application file for complete search history.

(56) References Cited

U.S. PATENT DOCUMENTS

| | | | |
|---|---|---|---|
| 3,242,186 A | 3/1966 | Dershowitz | |
| 3,785,813 A | 1/1974 | Rickter | |

(Continued)

FOREIGN PATENT DOCUMENTS

| | | |
|---|---|---|
| DE | 4121138 A1 | 1/1993 |
| DE | 197 44 792 A1 | 4/1999 |

(Continued)

OTHER PUBLICATIONS

Albert et al., Designing optical sensor arrays with enhanced sensitivity for explosives detection. Proceeedings of the SPIE—The International Society for Optical Engineering. Orlando, Florida. Apr. 13-17, 1998;3392(1-2):426-31. Abstract Only.

(Continued)

*Primary Examiner* — Shafiqul Haq
(74) *Attorney, Agent, or Firm* — Wolf, Greenfield & Sacks, P.C.

(57) ABSTRACT

The present invention provides materials, devices, and methods related to determination of an analyte. In some embodiments, an analyte may be determined by monitoring, for example, a change in an optical signal of a luminescent material (e.g., particle) upon exposure to an analyte. The present invention may be particularly advantageous in that some embodiments may comprise an emissive species useful as an internal reference standard. Methods of the invention may also be useful in the quantitative determination of an analyte. In some cases, the present invention may allow for selective determination of an analyte.

23 Claims, 17 Drawing Sheets

(56) References Cited

U.S. PATENT DOCUMENTS

| | | |
|---|---|---|
| 4,049,616 A | 9/1977 | Scott et al. |
| 4,356,429 A | 10/1982 | Tang |
| 4,513,078 A | 4/1985 | Sandrik et al. |
| 4,539,507 A | 9/1985 | VanSlyke et al. |
| 4,687,732 A | 8/1987 | Ward et al. |
| 4,752,588 A | 6/1988 | Ellis et al. |
| 4,839,112 A | 6/1989 | Wynne et al. |
| 4,841,099 A | 6/1989 | Epstein et al. |
| 4,868,103 A | 9/1989 | Stavrianopoulos et al. |
| 4,883,608 A | 11/1989 | Trujillo et al. |
| 4,894,443 A | 1/1990 | Greenfield et al. |
| 4,927,768 A | 5/1990 | Coughlin et al. |
| 4,946,890 A | 8/1990 | Meador |
| 4,957,615 A | 9/1990 | Ushizawa et al. |
| 4,992,244 A | 2/1991 | Grate |
| 4,992,302 A | 2/1991 | Lindmayer |
| 5,091,502 A | 2/1992 | Narang et al. |
| 5,155,149 A | 10/1992 | Atwater et al. |
| 5,157,261 A | 10/1992 | Gret et al. |
| 5,194,393 A | 3/1993 | Hugl et al. |
| 5,217,715 A | 6/1993 | Krivan et al. |
| 5,236,808 A | 8/1993 | Smothers |
| 5,237,582 A | 8/1993 | Moses |
| 5,244,813 A | 9/1993 | Walt et al. |
| 5,250,439 A | 10/1993 | Musho et al. |
| 5,254,633 A | 10/1993 | Han et al. |
| 5,312,896 A | 5/1994 | Bhardwaj et al. |
| 5,323,309 A | 6/1994 | Taylor et al. |
| 5,364,797 A | 11/1994 | Olson et al. |
| 5,387,462 A | 2/1995 | Debe |
| 5,414,069 A | 5/1995 | Cumming et al. |
| 5,451,663 A | 9/1995 | Kang et al. |
| 5,451,683 A | 9/1995 | Barrett et al. |
| 5,493,017 A | 2/1996 | Therien et al. |
| 5,511,547 A | 4/1996 | Markle et al. |
| 5,512,490 A | 4/1996 | Walt et al. |
| 5,512,635 A | 4/1996 | Nubel et al. |
| 5,532,129 A | 7/1996 | Heller |
| 5,540,999 A | 7/1996 | Yamamoto et al. |
| 5,546,889 A | 8/1996 | Wakita et al. |
| 5,549,851 A | 8/1996 | Fukushima et al. |
| 5,554,747 A | 9/1996 | Sharma et al. |
| 5,556,524 A | 9/1996 | Albers |
| 5,563,056 A | 10/1996 | Swan et al. |
| 5,565,322 A | 10/1996 | Heller |
| 5,580,527 A | 12/1996 | Bell et al. |
| 5,585,646 A | 12/1996 | Kossovsky et al. |
| 5,591,787 A | 1/1997 | Schlennert et al. |
| 5,597,890 A | 1/1997 | Jenekhe |
| 5,607,864 A | 3/1997 | Ricchiero et al. |
| 5,629,353 A | 5/1997 | Steckle, Jr. et al. |
| 5,674,698 A | 10/1997 | Zarling et al. |
| 5,674,751 A | 10/1997 | Jaduszliwer et al. |
| 5,675,001 A | 10/1997 | Hoffman et al. |
| 5,679,773 A | 10/1997 | Holmes |
| 5,700,696 A | 12/1997 | Chandross et al. |
| 5,705,348 A | 1/1998 | Meade et al. |
| 5,709,994 A | 1/1998 | Pease et al. |
| 5,710,187 A | 1/1998 | Steckle, Jr. et al. |
| 5,710,197 A | 1/1998 | Fischer et al. |
| 5,723,218 A | 3/1998 | Haugland et al. |
| 5,858,907 A | 1/1999 | Wang et al. |
| 5,869,592 A | 2/1999 | Gagné et al. |
| 5,925,517 A | 7/1999 | Tyagi et al. |
| 5,942,638 A | 8/1999 | Lichtenhan et al. |
| 5,998,204 A | 12/1999 | Tsien et al. |
| 6,020,426 A | 2/2000 | Yamaguchi et al. |
| 6,124,421 A | 9/2000 | Lau et al. |
| 6,254,829 B1 | 7/2001 | Hartmann et al. |
| 6,259,277 B1 | 7/2001 | Tour et al. |
| 6,303,733 B1 | 10/2001 | Lau et al. |
| 6,323,309 B1 | 11/2001 | Swager et al. |
| 6,328,932 B1 | 12/2001 | Carter et al. |
| 6,444,476 B1 | 9/2002 | Morgan |
| 6,444,479 B1 | 9/2002 | Choi |
| 6,469,123 B1 | 10/2002 | Lau et al. |
| 6,509,110 B1 | 1/2003 | Salbeck et al. |
| 6,556,335 B2 | 4/2003 | Lee et al. |
| 6,589,731 B1 | 7/2003 | Chen et al. |
| 6,605,693 B1 | 8/2003 | Becker et al. |
| 6,610,848 B1 | 8/2003 | Pilato et al. |
| 6,660,820 B1 | 12/2003 | Martin et al. |
| 6,670,645 B2 | 12/2003 | Grushin et al. |
| 6,713,298 B2 | 3/2004 | McDevitt et al. |
| 6,743,640 B2 | 6/2004 | Whitten et al. |
| 6,770,220 B1 | 8/2004 | Klimant |
| 6,783,814 B2 | 8/2004 | Swager et al. |
| 6,828,450 B2 | 12/2004 | Hua et al. |
| 6,830,828 B2 | 12/2004 | Thompson et al. |
| 6,835,835 B1 | 12/2004 | Huo |
| 6,902,830 B2 | 6/2005 | Thompson et al. |
| 6,919,139 B2 | 7/2005 | Grushin et al. |
| 6,946,688 B2 | 9/2005 | Grushin et al. |
| 6,962,757 B2 | 11/2005 | Epstein et al. |
| 7,001,536 B2 | 2/2006 | Thompson et al. |
| 7,029,765 B2 | 4/2006 | Kwong et al. |
| 7,041,910 B2 | 5/2006 | Swager et al. |
| 7,075,102 B2 | 7/2006 | Grushin et al. |
| 7,078,725 B2 | 7/2006 | Grushin et al. |
| 7,087,321 B2 | 8/2006 | Kwong et al. |
| 7,088,757 B1 | 8/2006 | Yu et al. |
| 7,098,060 B2 | 8/2006 | Yu et al. |
| 7,122,383 B2 | 10/2006 | Jones et al. |
| 7,129,518 B2 | 10/2006 | Grushin et al. |
| 7,186,355 B2 | 3/2007 | Swager et al. |
| 7,208,122 B2 | 4/2007 | Swager et al. |
| 7,250,519 B2 | 7/2007 | Stossel et al. |
| 7,291,503 B2 | 11/2007 | Swager |
| 7,393,503 B2 | 7/2008 | Swager et al. |
| 7,417,146 B2 | 8/2008 | Huo et al. |
| 7,462,325 B2 | 12/2008 | Hancock et al. |
| 7,521,232 B2 | 4/2009 | Moon |
| 7,662,309 B2 | 2/2010 | Swager et al. |
| 7,671,166 B2 | 3/2010 | Swager et al. |
| 7,759,127 B2 | 7/2010 | Rose et al. |
| 7,943,062 B2 | 5/2011 | Swager et al. |
| 8,158,437 B2 | 4/2012 | Swager et al. |
| 8,198,096 B2 | 6/2012 | Swager et al. |
| 8,283,423 B2 | 10/2012 | Swager et al. |
| 8,298,830 B2 | 10/2012 | Rose et al. |
| 8,367,001 B2 | 2/2013 | Swager et al. |
| 8,465,678 B2 | 6/2013 | Swager et al. |
| 2002/0040805 A1 | 4/2002 | Swager et al. |
| 2002/0051985 A1 | 5/2002 | Whitten et al. |
| 2002/0076830 A1 | 6/2002 | Mauze et al. |
| 2002/0137978 A1 | 9/2002 | Grubbs et al. |
| 2002/0150697 A1 | 10/2002 | Swager et al. |
| 2002/0150759 A1 | 10/2002 | Jones et al. |
| 2002/0177136 A1 | 11/2002 | McBranch et al. |
| 2003/0054413 A1 | 3/2003 | Kumaraswamy et al. |
| 2003/0096138 A1 | 5/2003 | Lecloux et al. |
| 2003/0134959 A1 | 7/2003 | Hancock et al. |
| 2003/0178607 A1 | 9/2003 | Swager et al. |
| 2004/0043251 A1 | 3/2004 | Epstein et al. |
| 2004/0089867 A1 | 5/2004 | Grushin et al. |
| 2004/0094768 A1 | 5/2004 | Yu et al. |
| 2004/0094769 A1 | 5/2004 | Grushin et al. |
| 2004/0106741 A1 | 6/2004 | Kriesel et al. |
| 2004/0116650 A1 | 6/2004 | Swager et al. |
| 2004/0121337 A1* | 6/2004 | Deans et al. .................. 435/6 |
| 2004/0170775 A1 | 9/2004 | Swager et al. |
| 2004/0175768 A1 | 9/2004 | Kushon et al. |
| 2004/0188673 A1 | 9/2004 | Grushin et al. |
| 2004/0197602 A1 | 10/2004 | Dobbs et al. |
| 2004/0235184 A1 | 11/2004 | Swager |
| 2004/0241768 A1 | 12/2004 | Whitten et al. |
| 2004/0254388 A1 | 12/2004 | Spreitzer et al. |
| 2005/0014160 A1 | 1/2005 | Kumaraswamy et al. |
| 2005/0037232 A1 | 2/2005 | Tyan et al. |
| 2005/0054854 A1 | 3/2005 | Stossel et al. |
| 2005/0059168 A1 | 3/2005 | Bazan et al. |
| 2005/0147534 A1 | 7/2005 | Swager et al. |
| 2005/0157261 A1 | 7/2005 | Hanebuchi et al. |
| 2005/0176624 A1 | 8/2005 | Thompson et al. |

(56) References Cited

U.S. PATENT DOCUMENTS

| | | |
|---|---|---|
| 2005/0186447 A1 | 8/2005 | Grushin et al. |
| 2005/0196775 A1 | 9/2005 | Swager et al. |
| 2005/0220714 A1 | 10/2005 | Kauzlarich et al. |
| 2005/0226775 A1 | 10/2005 | Aker et al. |
| 2005/0263758 A1 | 12/2005 | Treacher et al. |
| 2005/0285517 A1 | 12/2005 | Yu et al. |
| 2006/0024707 A1 | 2/2006 | Deans |
| 2006/0029829 A1 | 2/2006 | Deans et al. |
| 2006/0057425 A1 | 3/2006 | Grushin et al. |
| 2006/0058524 A1 | 3/2006 | Falcou et al. |
| 2006/0073607 A1 | 4/2006 | Rose et al. |
| 2006/0120917 A1 | 6/2006 | Swager et al. |
| 2006/0127929 A1 | 6/2006 | Swager et al. |
| 2006/0135772 A1 | 6/2006 | Huo |
| 2006/0173145 A1 | 8/2006 | Pawlow et al. |
| 2006/0270846 A1 | 11/2006 | Karpishin et al. |
| 2007/0081921 A1 | 4/2007 | Swager et al. |
| 2007/0083066 A1 | 4/2007 | Bohm et al. |
| 2009/0215189 A1 | 8/2009 | Swager et al. |
| 2010/0063225 A1 | 3/2010 | Swager et al. |
| 2010/0112715 A1 | 5/2010 | Swager et al. |
| 2010/0168352 A1 | 7/2010 | Arriola et al. |
| 2010/0213451 A1 | 8/2010 | Swager et al. |
| 2010/0310424 A1 | 12/2010 | Rose et al. |
| 2011/0142717 A1 | 6/2011 | Swager et al. |
| 2011/0175035 A1 | 7/2011 | Swager et al. |

FOREIGN PATENT DOCUMENTS

| | | |
|---|---|---|
| DE | 198 06 037 A1 | 9/1999 |
| EP | 0 259 951 | 3/1988 |
| EP | 0 442 123 A1 | 8/1991 |
| EP | 0 581 058 A1 | 2/1994 |
| EP | 0 748 805 A1 | 12/1996 |
| EP | 1 011 154 A1 | 6/2000 |
| JP | 06-322078 | 11/1994 |
| WO | WO 89/00593 | 1/1989 |
| WO | WO 95/16681 | 6/1995 |
| WO | WO-98/05693 A1 | 2/1998 |
| WO | WO 99/19419 A1 | 4/1999 |
| WO | WO 99/57222 | 11/1999 |
| WO | WO-00/05774 A1 | 2/2000 |
| WO | WO 00/53655 A1 | 9/2000 |
| WO | WO 01/57140 A1 | 8/2001 |
| WO | WO 02/16463 A2 | 2/2002 |
| WO | WO 02/074997 A1 | 9/2002 |
| WO | WO-02/079268 A2 | 10/2002 |
| WO | WO 03/048226 A2 | 6/2003 |
| WO | WO 2004/057014 A2 | 7/2004 |
| WO | WO-2005/030681 A1 | 4/2005 |
| WO | WO-2005/086617 A2 | 9/2005 |
| WO | WO 2006/081345 A1 | 8/2006 |
| WO | WO 2006/085319 A2 | 8/2006 |
| WO | WO 2008/019086 A2 | 2/2008 |
| WO | WO 2008/039529 A1 | 4/2008 |
| WO | WO-2008/042289 A2 | 4/2008 |
| WO | WO 2008/136805 A2 | 11/2008 |

OTHER PUBLICATIONS

Amara, J. et al., "Incorporation of Internal Free Volume: Synthesis and Characterization of Iptycene-Elaborated Poly(butadiene)s," Macromolecules 2004, 37, 3068-3070.

Arias-Marin et al., Amphiphilic Phenyl-Ethynylene Polymers and Copolymers. Synthesis, Characterization, and Optical Emission Properties. Macromolecules. 2003;36:3570-79.

Armengaud et al., "Electrochemistry of conducting polypyrrole films containing cobalt porphyrin," J. Electroanal. Chem., 1990, 277:197-211.

Audebert et al., "Description of New Redox and Conducting Polymers Based on Copper Containing Units; Emphasis on the Role of Copper in the Electron Transfer Mechanism," Synthetic Metals, 1991, 3049-3052.

Audebert et al., "Redox and Conducting Polymers Based on Salen-Type Metal Units; Electrochemical Study and Some Characteristics," New Journal of Chemistry, 1992 16(6):697-703.

Audebert et al., "Synthesis and Characteristics of New Redox Polymers Based on Copper Containing Units; Evidence for the Participation of Copper in the Electron Transfer Mechanism," New Journal of Chemistry, 1991, 15(4):235-237.

Bedioui et al., "Electrochemistry of conducting polypyrrole films containing cobalt porphyrin, Part 2. New Developments and inclusion of metallic aggregates in the coordination polymer," J. Electroanal. Chem., 1991, 297:257-269.

Bedioui et al., "Electrooxidative polymerization of cobalt, nickel and manganese salen complexes in acetonitrile solution," J. Electroanal. Chem., 1991, 301:267-274.

Bedioui et al., "Poly(Pyrrole-Manganese Tetraphenylporphyrin) film Electrodes in Acetonitrile Solution," J. Electroanal. Chem., 1988, 239:433-439.

Bettelheim et al., "Electrochemical Polymerization of Amino-, Pyrrole-, and Hydroxy-Substituted Tetraphenylporphyrins," Inorganic Chemistry, 1987, 26(7):1009-1017.

Bowyer et al., Electrochemical reduction of vicinal dinitro compounds. J Org Chem. 1988;53(22):5234-5239.

Brown et al., Fluorescence-enhancement sensing of ammonia and hydrazines via disruption of the internal hydrogen bond in a carbazolopyridinophane. Sensors Actuators B. 2005;110:8-12.

Bustin, Absolute quantification of mRNA using real-time reverse transcription polymerase chain reaction assays. J Mol Endocrinol. Oct. 2000;25(2):169-93.

Cameron et al., "A conjugated polymer/redox polymer hybrid with electronic communication between metal centres," Chem. Commun., 1997, 303-304.

Carrabba et al., Hydrogen bonding in the lowest singlet n-pi-star excited state of pyrimidine. J Phys Chem. 1985;89:674-77.

Chatterjee et al.,Synthesis of Functionalized Olefins by Cross and Ring-Closing Metatheses. J Am Chem Soc. 2000;122(15):3783-84.

Choi et al, Oxygen-sensitive reverse-phase optode membrane using silica gel-absorbed ruthenium(II) complex embedded in gelatin film. Anal. Chim. Acta 1999, 387, 197-205.

Cumming et al., "Using Novel Fluorescent Polymers as Sensory Materials for Above-Ground Sensing of Chemical Signature Compounds Emanating from Buried Landmines," IEEE Transactions on Geoscience and Remote Sensing, 2001, 39:1119-1128.

Dahm et al., "Catalytic Reduction of Iodoethane and 2-Iodopropane at Carbon Electrodes Coated with Anodically Polymerized Films of Nickel(II) Salen," Analytical Chemistry, 1994, 66(19):3117-3123.

Dai et al., Sensors and sensor arrays based on conjugated polymers and carbon nanotubes. Pure Appl Chem. 2002;74(9):1753-72.

Davey et al., New Rigid Backbone Conjugated Organic Polymers with Large Fluorescence Quantum Yields. J Chem Soc Chem Commun. 1995;1433-34.

Dijkstra et al., "Shape-Persistent Nanosize Organometallic Complexes: Synthesis and Application in a Nanofiltration Membrane Reactor," J. Org. Chem., 2003, vol. 68, No. 3, pp. 675-685.

Disney, M.D. et al., "Detection of Bacteria with Carbohydrate-Functionalized Fluorescent Polymers," J. Am. Chem. Soc. 2004, 126, 13343-13346.

Dudek et al., Synthesis and energy-transfer properties of hydrogen-bonded oligofluorenes. J Am Chem Soc. Aug. 24, 2005;127(33):11763-8.

Ellis et al., Conductive Polymer Films as Ultrasensitive Chemical Sensors for Hydrazine and Monomethylhydrazine Vapor. Anal Chem. 1996;68:817-22.

Erdogan et al., Synthesis and mesoscopic order of a sugar-coated poly(p-phenyleneethynylene). Macromolecules. 2002;35:7863-64.

European Search Report for EP 02024311.9 mailed Jan. 3, 2003.

Ewing et al., Detection of volatile vapors emitted from explosives with a handheld ion mobility spectrometer. Field Anal Chem Technol. 2001;5:215-21.

Famulok et al., Nucleic acid aptamers—from selection in vitro to applications in vivo. Acc Chem Res. Sep. 2000;33(9):591-9.

Funhoff et al., Cationic polymethacrylates with covalently linked membrane destabilizing peptides as gene delivery vectors. J Control Release. Jan. 3, 2005;101(1-3):233-46.

(56) References Cited

OTHER PUBLICATIONS

Garner, C., et al., "Challenges for dielectric materials in future integrated circuit technologies," Microelectronics Reliability 2005, 45, 919-924.
Goldsby et al., "Oxidation of Nickel(II) Bis(salicylaldimine) Complexes: Solvent Control of the Ultimate Redox Site," Polyhedron, 1989, 8(1):113-115.
Goldsby et al., "Symmetric and Unsymmetric Nickel(II) Schiff Base Complexes; Metal-Localized Versus Ligand-Localized Oxidation," J. Coord. Chem., 1988, 19:83-90.
Guimaraes et al., On the fluoresence of pyrrole derivative oligomer. Mater Sci Engineer C. 2008;28:1076-81.
Hard et al., Fluorescence studies of a single tyrosine in a type II DNA binding protein. Biochemistry. Jan. 10, 1989;28(1):396-406.
Havemann, R., "High-Performance Interconnects: An Integration Overview," Proceedings of the IEEE 2001, 89(5), 586-601.
Hoferkamp et al., "Surface-Modified Electrodes Based on Nickel(II) and Copper(II) Bis(salicylaldimine) Complexes," Chemistry of Materials, 1989, 1(3):348-352.
Horwitz et al., "Oxidative Electropolymerization of Metal Schiff-Base Complexes," Mol. Cryst. Liq. Cryst., 1988, 160:389-404.
Huang et al., Nanostructured polyaniline sensors. Chem Euro J. Mar. 19, 2004;10(6):1314-9.
International Search Report and Written Opinion mailed Feb. 23, 2006, PCT/US2005/033261.
International Preliminary Report on Patentability for PCT/US2005/033261 mailed Mar. 29, 2007.
Invitation to Pay Additional Fees for PCT/US2006/045390 mailed Jun. 12, 2007.
International Search Report and Written Opinion for PCT/US2006/045390 mailed Sep. 24, 2007.
International Preliminary Report on Patentability for PCT/US2006/045390 mailed Jun. 5, 2008.
Invitation to Pay Additional Fee for PCT/US2007/017380 mailed Jan. 4, 2008.
International Search Report and Written Opinion mailed Apr. 8, 2008 in PCT/US2007/017380.
International Preliminary Report on Patentability mailed Nov. 10, 2008 in PCT/US2007/017380.
International Search Report and Written Opinion mailed Dec. 14, 2007 in PCT/US2007/020961.
International Preliminary Report on Patentability dated Mar. 31, 2009, mailed Apr. 9, 2009, in PCT/US2007/020961.
Invitation to Pay Additional Fee for PCT/US2007/020992 mailed Feb. 8, 2008.
International Search Report and Written Opinion for PCT/US2007/020992 mailed Apr. 4, 2008.
International Preliminary Report on Patentability for PCT/US2007/020992 mailed Apr. 9, 2009.
International Search Report and Written Opinion mailed Oct. 27, 2008 in PCT/US2007/022670.
International Preliminary Report on Patentability dated Apr. 28, 2009, mailed May 7, 2009, in PCT/US2007/022670.
Invitation to Pay Additional Fee for PCT/US2007/021370 mailed Feb. 22, 2008.
International Search Report and Written Opinion mailed Jun. 13, 2008 in PCT/US2007/021370.
International Preliminary Report on Patentability for PCT/US2007/021370 mailed Apr. 16, 2009.
Jensen et al., Cytoplasmic delivery and nuclear targeting of synthetic macromolecules. J Control Release. Feb. 21, 2003;87(1-3):89-105.
Katayama et al., Vinylideneruthenium complexes in catalysis. Coord Chem Revs. 2004;248:1703-15.
Li et al., Water-Soluble Poly(acrylic acid) Grafted Luminescent Silicon Nanoparticles and Their Use as Fluorescent Biological Staining Labels. Nano Letters. 2004; 4(8):1463-1467.
Lim et al., Transferrin-oligomers as potential carriers in anticancer drug delivery. Pharm Res. Nov. 2004;21(11):1985-92.

Long, T. et al., "Molecular Design of Free Volume as a Route to Low-k Dielectric Materials," J. Am. Chem. Soc. 2003, 125, 14113-14119.
MacDiarmid, Polyanaline and polypyrrole: Where are we headed? Synthetic Metals. 1997;84:27-34.
Maex, K. et al., "Low dielectric constant materials for microelectronics," Journal of Applied Physics 2003, 93(11), 8793-841.
Maier, G., "Low dielectric constant polymers for microelectronics," Prog. Polym. Sci. 2001, 26, 3-65.
Martin, S. et al., "Development of a Low-Dielectric-Constant Polymer for the Fabrication of Integrated Circuit Interconnect," Adv. Mater. 2000, 12(23), 1769-78.
Matloka et al., The acyclic diene metatheis (ADMET) polymerization approach to silicon containing materials. J Mol Catalysis. 2006;257:89-98.
Mañes et al., Extraction-spectrophotometric determination of hydrazine with 2-hydroxy-1-naphthaldehyde. Analyst. 1987;112:1183-84.
Moisy et al., "Epoxidation of cis-cyclooctene by Molecular Oxygen Electrocatalysed by Polypyrrole-Manganese Porphyrin Film Modified Electrodes," J. Electroanal. Chem., 1988, 250:191-199.
Moon et al., Live-cell-permeable poly(p-phenylene ethynylene). Angew Chem Int Ed Engl. 2007;46(43):8223-5.
Morgen, M., et al., "Low Dielectric Constant Materials for ULSI Interconnects," Annu. Rev. Mater. Sci. 2000, 30, 645-80.
Moroni et al., Rigid Rod Conjugated Polymers for Nonlinear Optics. 3. Intramolecular H Bond Effects on Poly(phenyleneethynylene) Chains. Macromolecules. 1997;30:1964-72.
Murarka, S., "Materials aspects of copper interconnection technology for semiconductor applications," Materials Science and Technology 2001, 17, 749-58.
Ng et al., Syntheses and characterisation of electrically conductive and fluorescent poly[3-(ω-bromoalkyl)thiophenes]. Synthetic Metals. 1999;100:269-77.
Office Action from U.S. Appl. No. 11/252,419 dated Mar. 13, 2008.
Office Action from U.S. Appl. No. 11/252,419 dated Dec. 12, 2008.
Office Action from U.S. Appl. No. 11/252,419 dated Jun. 12, 2009.
Okamoto, I. et al., "Orbital Unsymmetrization Affects Facial Selectivities of Diels-Alder Dienophiles," J. Org. Chem. 1996, 61, 3155-3166.
Ortega-Barrales et al., Solid-phase spectrophotometric determination of trace amounts of hydrazine at sub-ng ml-1 level. Anal Chim Acta. 1997;353:115-22.
Orynbayeva et al., Visualization of membrane processes in living cells by surface-attached chromatic polymer patches. Angew Chem Int Ed Engl. Feb. 4, 2005;44(7):1092-6.
Osborne et al., Nucleic Acid Selection and the Challenge of Combinatorial Chemistry. Chem Rev. Apr. 1, 1997;97(2):349-370.
Pei et al., First Hydrogen-Bonding-Induced Self-Assembled Aggregates of a Polyfluorene Derivative. Macromolecules. 2003;36:323-27.
Pei et al, Polymer Light-Emitting Electrochemical Cells: In Situ Formation of a Light-Emitting p-n Junction. J Am Chem Soc. 1996;118(16):3922-3929.
Perr et al., Solid phase microextraction ion mobility spectrometer interface for explosive and taggant detection. J Sep Sci. Feb. 2005;28(2):177-83.
Pingarron et al., Carbon fibre microelectrodes modified with rhodium for the electrocatalytic determination of hydrazine. Anal Chim Acta. 2001;439:281-90.
Ratcliffe, Polypyrrole-based sensor for hydrazine and ammonia. Anal Chim Acta. 1990;239:257-62.
Reddinger et al., "Electroactive π-Conjugated Polymers Based on Transition Metal-Containing Thiophenes Capable of Sensing Ionic and Neutral Species," ACS Polym. Prepr., 1997, 321-322.
Reddinger et al., "Electroactive π-Conjugated Polymers Based on Transition Metal-Containing Thiophenes," Synthetic Metals, 1997, 84:225-226.
Reddinger et al., "Tunable Redox and Optical Properties Using Transition Metal-Complexed Complexed Polythiophenes," Macromolecules, 1997, 30(3):673-675.
Rose et al., Sensitivity gains in chemosensing by lasing action in organic polymers. Nature. Apr. 14, 2005;434(7035):876-9.

(56) References Cited

OTHER PUBLICATIONS

Rose et al., "Excited-State Lifetime Modulation in Triphenylene-Based Conjugated Polymers," J. Am. Chem. Soc., 2001, 123:11298-11299.
Schwarz et al., "Spectroscopic Studies of Cyclometalated Platinum(II) Complexes: Optical Absorption and Emission of Single-Crystal cis-Bis(benzo[h]guinolinato)platinum(II)," Inorg. Chem. 1989, 28, 1053-59.
Segawa et al., "Approaches to conducting polymer devices with nano-structure: Electrochemical construction of one-dimensional and two-dimensional prophyrin-oligothiophene co=polymers," Synthetic Metals, 1995, 71:2151-2154.
Shabani et al., Indirect Spectrophotometric Determination of Trace Quantities of Hydrazine. Bull Korean Chem Soc. 2004;25:213-15.
Shamiryan, D. et al., "Low-κ dielectric materials," Materials Today, Jan. 2004. 34-39.
Shimidzu et al., "Approaches to conducting polymer devices with nanostructures: photoelectrochemical function of one-dimensional and two-dimensional porphyrin polymers with oligothienyl molecular wire," Journal of Photochemistry and Photobiology A: Chemistry 99, 1995, Article 4168:1-7.
Smet, M. et al., "Synthesis of the Formal Diels-Alder Adducts of N-substituted Dehydromaleimides and Anthracene," Molecules 2000, 5, 179-188.
Treichel, H. et al., "Integration Challenges for Low Dielectric Constant Materials," Advanced Engineering Materials. 2001;7(3):461-64.
Tsai et al., New Thiophene-Linked Conjugated Poly(azomethine)s: Theoretical Electronic Structure, Synthesis, and Properties. Macromolecules. 2005;38:1958-66.
Vilas-Boas et al., "New Insights into the Structure and Properties of Electroactive Polymer Films Derived from [Ni(salen)]," Inorganic Chemistry, 1997, 36(22):4919-4929.
Virji et al., Hydrazine Detection by Polyaniline Using Fluorinated Alcohol Additives. Chem Mater. 2005;17(5):1256-1260.
Virji et al., Polyaniline Nanofiber Gas Sensors: Examination of Response Mechanisms. Nano Letters. 2004;4(3):491-496.
Von Zelewsky et al., "Thermal and Photochemical Oxidative Addition of Alkyl Halides to the Cyclometalated Complex cis-Bis[2-(2'-thienyl)pyridine]platinum(II)," Inorg. Chem. 1993, 32, 4585-93.
Wang et al., Catalytic-adsorptive stripping voltammetric measurements of hydrazines. Talanta. Dec. 1988;35(12):965-8.
Wang et al., Hydrazine Detection Using a Tyrosinase-Based Inhibition Biosensor. Anal Chem. 1995;67:3824-27.
Wu et al., Novel water-soluble fluorescent polymer containing recognition units: Synthesis and interactions with PC12 cell. Euro Polymer J. 2005;41:1985-1992.
Yamaguchi et al., Light-emitting efficiency tuning of rod-shaped pi conjugated systems by donor and acceptor groups. J Am Chem Soc. Jul. 6, 2005;127(26):9332-3.
Yang et al.,Growth of Ultrathin Covalently Attached Polymer Films: Uniform Thin Films for Chemical Microsensors. Langmuir. 1998;14:1505-07.
Yu et al., New efficient blue light emitting polymer for light emitting diodes. Chem Commun. 1999:1837-38.
Yuan et al., +Fiber optic chemical sensors using a modified conducting polymer cladding . SPIE. 2001;4205:170-79.
Zahn et al., "Three-Dimensional Electronic Delocalization in Chiral Conjugated Polymers," Angew. Chem. Int. Ed. Engl., 2002, 41(22):4226-4230.
Zhang et al., Fluorescent detection of chemical warfare agents: functional group specific ratiometric chemosensory. J Am Chem Soc. Mar. 26, 2003;125(12):3420-1.
Zheng et al., Biotinylated poly(p-phenylene ethynylene): unexpected energy transfer results in the detection of biological analytes. Chem Commun (Camb). Dec. 21, 2004;(24):2798-9. Epub Nov. 4, 2004.
Zheng, J. et al., Supporting Information for "Energy Transfer from Biotinylated Poly)p-phenylene ethynylene): New Insights for Amplified Fluorescence-Based Biosensors" [Chem. Commun., 2004, 2798-2799].
Zhou et al., Novel Polyphenylenes Containing Phenol-Substituted Oxadiazole Moieties as Fluorescent Chemosensory for Fluoride Ion. Macromolecules. 2005;38:2148-53.
Zhu et al., "Conducting Polymetallorotaxanes: A Supramolecular Approach to Transition Metal Ion Sensors," Journal of the American Chemical Society, 1996, 118(36):8713-8714.
Zhu et al., "Design of Conducting Redox Polymers: A Polythiophene-Ru(bipy)3n Hybrid Material," Adv. Mater., 1996, 8(6):497-500.
Zotti et al., "Conductivity in Redox Modified Conducting Polymers. 2. Enhanced Redox Conductivity in Ferrocene-Substituted Polypyrroles and Polythiophenes," Chem. Mater., 1995 7(12):2309-2315.
Abraham et al., "Hydrogen bonding. Part 29. Characterization of 14 Sorbent Coatings for Chemical Microsensors using a New Solvation Equation," J. Chem. Soc. Perkin Trans., 1995, 2, 369-378.
Achyuthan et al., "Fluorescence superquenching of conjugated polyelectrolytes: applications for biosensing and drug discovery," J. Mater. Chem., 2005, 15, 2648-2656.
Amara et al., "Synthesis and Properties of Poly(phenylene ethynylene)s with Pendant Hexafluoro-2-propanol Groups," Macromolecules, 2005, 38, 9091-9094.
Baldo et al., "Excitonic singlet-triplet ratio in a seminconducting organic thin film," Phys. Rev. B., 1999, 60(20), 14422-14428.
Baldo et al., "High-efficiency fluorescent organic light-emitting devices using a phosphorescent sensitizer," Nature, 2000, 403, 750-753.
Barigelletti et al., "Temperature Dependence of the Luminscence of Cyclometalated Palladium(II), Rhodium(III), Platinum(II), and Platinum(IV) Complexes," Inorg. Chem., 1988, 27(20), 3644-3647.
Bergstedt et al., "Superquenching of Fluorescent Polyelectrolytes and its Applications for Chemical and Biological Sensing," Proceedings of SPIE, 2001, 4279, 94-100.
Brabec et al., "Plastic Solar Cells," Adv. Funct. Mater, 2001, 11(1), 15-26.
Bredas et al., "Electronic Structure of Poly(paraphenylene vinylene): Influence of Copolymerization and Derivatization on Light-Emitting Characteristics," Am. Chem. Scoc., Div. Polym. Chem., 1994, 35, 185-186.
Brooks et al., "Synthesis and Characterization of Phosophorescent Cyclometalated Platinum Complexes," Inorg. Chem., 2002, 41(12), 3055-3066.
Brown et al., "Core-referenced ratiometric fluorescent potassium ion sensors using self-assembled ultrathin films on europium nanoparticles," IEEE Sensors Journal, 2005, 5(6), 1197-1205.
Cabarcos et al., "Effect of the Molecular Weight and the Ionic Strength on the Photoluminescence Quenching of Water-Soluble Conjugated Polymer Sodium Poly[2-(3-thienyl)ethyloxy-4-butylsulfonate]," Macromolecules, 2005, 38(25), 10537-10541.
Chassot et al., "cis-Bis(2-phenylpyridine platinum(II)(CBPPP): A Simple Molecular Platinum Compound," Inorg. Chem., 1984, 23(25), 4249-4253.
Chassot et al., "Photochemical Preparation of Luminsecent Platinum(IV) Complexes via Oxidative Addition on Luminescent Platinum(II) Complexes," J. Am. Chem. Soc., 1986, 108, 6084-6085.
Chassot et al., "Cyclometalated Complexes of Platinum(II): Homoleptic Compounds with Aromatic C,N Ligands," Inorg. Chem., 1987, 26(17), 2814-2818.
Chen et al., "Highly Sensitive Biological and Chemical Sensors Based on Reversible Fluorescence Quenching in a Conjugated Polymer," Proceedings of the National Academy of Sciences of the United States of America, 1999, 96(22), 12287-12292.
Chen et al., "Surfactant-induced modification of quenching of conjugated polymer fluorescence by electron acceptors: applications for chemical sensing," Chemical Physics Letters, 2000, 330, 27-33.
Chen et al., "Tuning the properties of conjugated polyelectrolytes through surfactant complexation," J. Am. Chem. Soc., 2000, 122(38), 9302-9303.
Costa-Fernandez et al., "Sol-gel immobilized room-temperature phosphorescent metal-chelate as luminescent oxygen sensing material," Anal. Chim. Acta., 1998, 360, 17-26.
Cotts et al., "Equilibrium Flexibility of a Rigid Linear Conjugated Polymer," Macromolecules, 1996, 29, 7323-7328.
Dagani, "A Better Sensor for Nerve Gas," C&EN, Mar. 10, 2003, 12.

(56) References Cited

OTHER PUBLICATIONS

Deans et al., "A Poly(p-phenyleneethynylene) with a Highly Emissive Aggregated Phase," *J. Am. Chem. Soc.*, 2000, 122(35), 8565-8566.

Decher, "Fuzzy Nanoassemblies: Toward Layered Polymeric Multicomposites," *Science*, 1997, 277(5330), 1232-1237.

Demchenko et al., "The problem of self-calibration of fluorescence signal in microscale sensor systems," *Lab on a Chip*, 2005, 5, 1210-1223.

Deng et al., "Direct Observation of the 'Pac-Man' Effect from Dibenzofuran-Bridged Cofacial Bisporphyrins," *J. Am. Chem. Soc.*, 2000, 122(2), 410-411.

Dougherty et al., "Photodynamic Therapy," *J. Natl. Cancer Inst.*, 1998, 90(12), 889-905.

Dwight et al., "Perturbation of Fluorescence by Nonspecific Interactions between Anionic Poly(phenylenevinylene)s and Proteins: Implications for Biosensors," *J. Am. Chem. Soc.*, 2004, 126(51), 16850-16859.

Fan et al., "Beyond superquenching: hyper-efficient energy transfer from conjugated polymers to gold nanoparticles," *PNAS*, 2003, 100(11), 6297-6301.

Fan et al., "High Efficiency Fluorescence Quenching of Conjugated Polymers by Proteins," *J. Am. Chem. Soc.*, 2002, 124(20), 5642-5643.

Fan et al., "Photoluminescence Quenching of Water-Soluble Conjugated Polymers by Viologen Derivatives: Effect of Hydrophobicity," *Langmuir*, 2003, 19(8), 3554-3556.

Fiesel et al., "A chiral poly(para-phenyleneethynylene) (PPE) derivative," *Macromol. Rapid Commun.*, 1998, 19(8), 427-431.

Fiesel et al., "Aggregation-induced CD effects in chiral poly(2,5-dialkoxy-1,4-phenylene)s," *Acta Polym.*, 1998, 49, 445-449.

Fiesel et al., "On the Solid State Aggregation of Chiral Substituted Poly(para-phenylene)s (PPPs)," *Synthetic Metals*, 1999, 102, 1457-1458.

Fu et al., "Alternating Poly(PyridylVinylenePhenyleneVinylene)s: Synthesis and Solid State Organizations," *Tetrahedron*, 1997, 53(45), 15487-15494.

Gaylord et al., "DNA detection using water-soluble conjugated polymers and peptide nucleic acid probes," *PNAS*, 2002, 99(17), 10954-10957.

Gaylord et al., "DNA Hybridization Detection with Water-Soluble Conjugated Polymers and Chromophore-Labeled Single-Stranded DNA," *J. Am. Chem. Soc.*, 2003, 125(4), 896-900.

Gaylord et al., "SNP Ddetection using peptide nucleic acid probes and conjugated polymers: Application in neurodegenerative disease identification," *PNAS*, 2005, 102(1), 34-39.

Gaylord et al., "Water-Soluble Conjugated Oligomers: Effect of Chain Length and Aggregation on Photoluminescence-Quenching Efficiencies," *Journal of the American Chemical Society*, 2001, 123(26), 6417-6418.

Gianini et al., "Square Planar (SP-4) and Octahedral (OC-6) Complexes of Platinum (II) and -(IV) with Predetermined Chirality at the Metal Center," *Inorg. Chem.*, 1996, 35(17), 4889-4895.

Gianini et al., "Chiral Cyclometalated Platinum(II) Complexes with Derivatives of Thienylpyridine as Ligands: Helical Distortion of the Square Planar (SP-4) Geometry," *Inorg. Chem*, 1997, 36(26), 6094-6098.

Goldfinger et al., "Fused polycyclic aromatics via electrophile-induced cyclization reactions: application to the synthesis of graphite ribbons," *J. Am. Chem. Soc.*, 1994, 116(17), 7895-7896.

Grate et al., "Hydrogen Bond Acidic Polymers for Surface Acoustic Wave Vapor Sensors and Arrays," *Anal. Chem.*, 1999, 71(5), 1033-1040.

Grate, "Acoustic Wave Microsensor Arrays for Vapor Sensing," *Chem Rev.*, 2000, 100(7), 2627-2648.

Guice et al., "Nanoscale internally referenced oxygen sensors produced from self-assembled nanofilms on fluorescent nanoparticles," *Journal of Biomedical Optics*, 2005, 10(6), 064031.

Halkyard et al., "Evidence of Aggregate Formation for 2,5-Dialkylpoly (p-phenyleneethynylenes) in Solution and Thin Films," *Macromolecules*, 1998, 31(25), 8655-8659.

Harrison et al., "Amplified Fluorescence Quenching in a Poly(p-phenylene)-Based Cationic Polyelectrolyte," *J. Am. Chem. Soc.*, 2000, 122(35), 8561-8562.

Heeger et al., "Making Sense of Polymer-Based Biosensors," *PNAS*, 1999, 96(22), 12219-12221.

Herbich et al. "Fluorescence Quenching by Pyridine and Derivatives Induced by Intermolecular Hydrogen Bonding to Pyrrole-Containing Heteroaromatics," *J. Phys. Chem. A.*, 2002, 106(10), 2158-2163.

Hill et al., "A Mechanistic Study of the Photochemically Initiated Oxidative Addition of Isopropyl Iodide to Dimethl(1,10-phenanthroline)platinum(II)," *J. Am. Chem. Soc.*, 1985, 107(5), 1218-1225.

Hoffmeister et al., "Triptycene Polymers," *J. Polymer Science Part A-1*, 1969, 7, 55-72.

Höger et al., "Synthesis, Aggregation, and Adsorption Phenomena of Shape-Persistent Macrocycles with Extraannular Polyalkuly Substituents," *J. Am. Chem. Soc.*, 2001, 123(24), 5651-5659.

Houk et al., "[C—H•••O] Interactions as a Control Element in Supramolecular Complexes: Experimental and Theoretical Evaluation of Receptor Affinities for the Binding of Bipyridinium-Based Guests by Catenated Hosts," *J. Am. Chem. Soc.*, 1999, 121(7), 1999, 1479-1487.

Houser et al., "Rational materials design of sorbent coatings for explosives: applications with chemical sensors," *Talanta*, 2001, 54, 469-485.

Huang et al., "Design of a Modular-Based Fluorescent Conjugated Polymer for Selective Sensing," *Angew. Chem. Int. Ed.*, 2004, 43(42), 5635-5638.

Jayarahjah et al., "Oxygen Diffusion and Permeability in Alkylaminothionylphosphazene Films Intended for Phosphorescence Barometry Applications," *Macromolecules*, 2000, 33(15), 5693-5701.

Jolliet et al., "Cyclometalated Complexes of Palladium(II) and Platinum(II): cis-Configured Homoleptic and Heteroleptic Compounds with Aromatic CN Ligands," *Inorg. Chem.*, 1996, 35(17), 4883-4888.

Joly et al., "Highly Effective Water-Soluble Fluorescence Quenchers of Conjugated Polymer Thin Films in Aqueous Environments," *Macromolecules*, 2006, 39(21), 7175-7177.

Jones et al., "Building highly sensitive dye assemblies for biosensing from molecular building blocks," *PNAS*, 2001, 98(26), 14769-14772.

Jones et al., "Superquenching and Its Applications in J-Aggregated Cyanine Polymers," *Langmuir*, 2001, 17(9), 2568-2571.

Jones et al., "Tuning of superquenching in layered and mixed fluorescent polyelectrolytes," *JACS*, 2001, 123(27), 6726-6727.

Kim et al. "A Fluorescent Self-Amplifying Wavelength-Responsive Sensory Polymer for Fluoride Ions," *Angew. Chem. Int. Ed*, 2003, 42, 4803-4806.

Kim et al. "Nonspecific Interactions of a Carboxylate-Substituted PPE with Proteins. A Cautionary Tale for Biosensor Applications," *Langmuir*, 2005, 21(17), 7985-7989.

Kim et al., "Control of conformational and interpolymer effects in conjugated polymers," *Nature*, 2001, 411, 1030-1034.

Kim et al., "Directing Energy Transfer within Conjugated Polymer Thin Films," *J. Am. Chem. Soc.*, 2001, 123(46), 11488-11489.

Kim et al., "Ion-Specific Aggregation in Conjugated Polymers: Highly Sensitive and Selective Fluorescent Ion Chemosensors," *Agnew Chem. Int. Ed.*, 2000, 39(21), 3868-3872.

Kim et al., "Structural Control in Thin Layers of Poly)P-phenyleneethynylene)s: Photophysical Studies of Langmuir and Langmuir-Blodgett Films," *J. Am. Chem. Soc.*, 2002, 124(26), 7710-7718.

Kim et al., "Ultrafast Energy-Transfer Dynamics between Block Copolymer and π-Conjugated Polymer Chains in Blended Polymeric Systems," *Chemistry of Materials*, 13(8), 2666-2674.

(56) References Cited

OTHER PUBLICATIONS

Köhler et al., "Novel Chiral Macrocycles Containing Two Electronically Interacting Arylene Chromophores," *Chem. Eur. J.*, 2001, 7(14), 3000-3004.

Kraft et al., "Electroluminescent Conjugated Polymers—Seeing Polymers in a New Light," *Agnew. Chem. Int. Ed.*, 1998, 37, 402-428.

Kui et al., "Structures, Photoluminescence, and Reversible Vapoluminescence Properties of Neutral Platinum(II) Complexes Containing Extended π-Conjugated Cyclometalated Ligands," *J. Am. Chem. Soc.*, 2006, 128(25), 8297.

Kumaraswamy et al., "Fluorescent-conjugated polymer superquenching facilitates highly sensitive detection of proteases," *PNAS*, 2004, 101(20), 7511-7515.

Kushon et al., "Detection of DNA Hybridization via Fluorescent Polymer Superquenching," *Langmuir, The ACS Journal of Surfaces and Colloids*, 2002, 18(20), 7245-7249.

Kushon et al., "Detection of single nucleotide mismatches via fluorescent polymer superquenching," *Langmuir*, 2003, 19(16), 6456-6464.

Lamansky et al., "Highly Phosphorescent Bis-Cyclometalated Iridium Complexes: Synthesis, Photophysical Characterization, and Use in Organic Light Emitting Diodes," *J. Am. Chem. Soc.*, 2001, 123(18), 4304-4312.

Lamba et al., "Imine-Bridged Planar Poly(*p*-phenylene) Derivatives for Maximization of Extended π-Conjugation. The Common Intermediate Approach," *J. Am. Chem. Soc.*, 1994, 116(26), 11723-11736.

Langveld et al., "Circular Dichroism and Circular Polarization of Photoluminescence of Highly Ordered Poly{3,4-di[(*S*)-2-methylbutoxy]thiophene}," *J. Am. Chem. Soc.*, 1996, 118(20), 4908-4909.

Levitsky et al., "Energy Migration in a Poly(phenylene ethynylene): Determination of Interpolymer Transport in Anistropic Langmuir-Blodgett Films," *J. Am. Chem. Soc.*, 1999, 121(7), 1466-1472.

Levitsky et al., "Mass and Energy Transport in Conjugated Polymer Langmuir-Blodgett Films; Conductivity, Fluorescence, and UV-Vis Studies," *Macromolecules*, 2001, 34(7), 2315-2319.

Levitsky et al., "Rational Design of a Nile Red/Polymer Composite Film for Fluorescence Sensing of Organophosphonate Vapors Using Hydrogen Bond Acidic Polymers," *Anal. Chem.*, 2001, 73(14), 3441-3448.

Levitsky et al., "Signal Amplification in Multichromophore Luminescence-Based Sensors," *J. Phys. Chem. B*, 2001, 105(35), 8468-8473.

Li et al., "Novel Surfactant-Free Stable Colloidal Nanoparticles Made of Randomly Carboxylated Polystyrene Ionomers," *Macromolecules*, 1997, 30(7), 2201-2203.

Liao et al., "Quantification of Amplified Quenching for Conjugated Polymer Microsphere Systems," *Langmuir*, 2007, 23(1), 112-115.

Lipkowitz et al., "A protocol for determining enantioselective binding of chiral analytes on chiral chromatographic surfaces," *Journal of the American Chemical Society*, 1988, 110(11), 3446-3452.

Liu et al., "Effect of Chromophore-Charge Distance on the Energy Transfer Properties of Water-Soluble Conjugated Oligomers," *J. Am. Chem. Soc.*, 2003, 125(22), 6705-6714.

Liu et al., "Fluorescence Quenching Mechanism of a Polyphenylene Polyelectrolyte with Other Macromolecules: Cytochrome c and Dendrimers," *Langmuir*, 2005, 21(5), 1687-1690.

Liu et al., "Homogeneous Fluorescence-Based DNA Detection with Water-Soluble Conjugated Polymers," *Chem Mater*, 2004, 16(23), 4467-4476.

Liu et al., "Methods for Strand-Specific DNA Detection with Cationic Conjugated Polymers Suitable for Incorporation into DNA Chips and Microarrays," *PNAS*, 2005, 102(3), 589-593.

Liu et al., "Optimization of the Molecular Orbital Energies of Conjugated Polymers for Optical Amplification of Fluorescent Sensors," *JACS.J. Am. Chem. Soc.*, 2006, 128(4), 1188-1196.

Lu et al., "'Cyanine Pendant' Polymers on Nanoparticles and in Solution; Superquenching and Sensing Applications," *Polym. Mat. Sci. Eng.*, Dept. of Chem. and Biochem., Arizona State University, 2002, 86, 17-18.

Lu et al., "Biocidal Activity of a Light-Absorbing Fluorescent Conjugated Polyelectrolyte," *Langmuir*, 2005, 21, 10154-10159.

Lu et al., "Self-Assembled 'Polymers' on Nanoparticles: Superquenching and Sensing Applications," Dept. of Chem. and Biochem., Arizona State University.*Polymer Preprints*, 2002, 43, 124-125.

Lu et al., "Superquenching in Cyanine Pendant Poly($_L$-lysine) Dyes: Dependence on Molecular Weight, Solvent, and Aggregation," *J. Am. Chem. Soc.*, 2002, 124(3), 483-488.

Lu et al., "Surface-Enhanced Superquenching of Cyanine Dyes as J-Aggregates on Laponite Clay Nanoparticles," *Langmuir*, 2002, 18(20), 7706-7713.

Luo et al., "Thermodynamic Stabilization Mechanism of Block Copolymer Vesicles," *Journal of the American Chemical Society*, 2001, 123(5), 1012-1013.

Maestri et al., "Absorption Spectra and Luminescence Properties of Isomeric Platinum(II) and Palladium(II) Complexes Containing 1,1'-Biphenyldiyl, 2-Phenylpyridine, and 2, 2'-Bipyridine as Ligands," *Helvetica Chimica Acta*, 1988, 71, 1053-1059.

Martin et al., "Picosecond Laser Photolysis Studies of Deactivation Processes of Excited Hydrogen-Bonding Complexes. 2. Dibenxocarbazole-Pyridine Systems," *J. Phys. Chem.*, 1982, 86(21), 4148-4156.

McGill et al., "Choosing polymer coatings for chemical sensors," *Chemtech*, 1994, 24, 27-37.

McQuade et al., "Conjugated Polymer-Based Chemical Sensors," *Chem. Rev.*, 2000, 100(7), 2537-2574.

McQuade et al., "Two-Dimensional Conjugated Polymer Assemblies: Interchain Spacing for Control of Photophysics," *J. Am. Chem. Soc.*, 2000, 122(24), 5885-5886.

Medintz et al., "Quantum dot bioconjugates for imaging, labelling and sensing," *Nature Materials*, 2005, 4(6), 435-446.

Miao et al., "Fluorescence Sensory Polymers Containing Rigid Nonplanar Aromatic Scaffolds," Proceedings of the 1997 Boston meeting, vol. 39, No. 2, pp. 1081-1082, Aug. 23-27, 1998, Polym. Prepr. Div. Polym. Chem. Am. Chem. Soc.; Polymer Preprints, Division of Polymer Chemistry, American Chemical Society, Aug. 1998 ACS, Washington D.C.

Mitschke et al., "The electroluminescence of organic materials," *J. Mater. Chem.*, 2000, 10(5-8), 1471-1507.

Miyasaka et al., "Femtosecond-Picosecond Laser Photolysis Studies on the Mechanisms of Fluorescence Quenching Induced by Hydrogen-Bonding Interactions—1-Pyrenol-Pyridine Systems," *J. Phys. Chem.*, 1993, 97(31), 8222-8228.

Moon et al., "Capture and detection of a quencher labeled oligonucleotide by poly)phenylene ethynylene) particles," *Chem. Commun.*, 2003, 1, 104-105.

Morin et al., "Syntheses of Conjugated Polymers Derived from N-Alkyl-2,7-carbazoles," *Macromolecules*, 2001, 34(14), 4680-4682.

Nie et al., "Immobilization of polydiacetylene onto silica microbeads for colorimetric detection," *J. Mater. Chem.*, 2006, 16, 546-549.

Norvez et al., "Epitaxygens: mesomorphic properties of triptycene derivatives," *Liquid Chemicals Crystals*, 1993, 14(5), 1389-1395.

Oda et al., "Chiroptical properties of chiral-substituted polyfluorenes," *Synthetic Metals*, 2000, 111-112, 575-577.

Oda et al., "Circularly Polarized Electroluminescence from Liquid-Crystalline Chiral Polyfluorenes," *Advanced Materials*, 2000, 12(5), 362-365.

Ow et al., "Bright and stable core-shell fluorescent silica nanoparticles," *Nano Letters*, 2005, 5(1), 113-117.

Park et al., "Ratiometric Optical PEBBLE Nanosensors for Real-Time Magnesium Ion Concentrations Inside Viable Cells," *Anal. Chem.*, 2003, 75(15), 3784-3791.

Patel, et al., "Chemicapacitive microsensors for volatile organic compound detection," *Sensors and Actuators B*, 2003, 96, 541-553.

Peeters et al., "Circularly Polarized Electroluminescence from a Polymer Light-Emitting Diode," *J. Am. Chem. Soc.*, 1997, 119(41), 9909-9910.

Peng et al., "Efficient Light Harvesting by Sequential Energy Transfer across Aggregates in Polymers of Finite Conjugational Segments with short Aliphatic Linkages," *J. Am. Chem. Soc.*, 2001, 123(46), 11388-11397.

(56) References Cited

OTHER PUBLICATIONS

Pinnaduwage et al., "Detection of 2,4-dinitrotoluene using microcantilever sensors," *Sensors and Actuators B*, 2004, 99, 223-229.
Pisaravskii et al., "Fluoresence spectrum and quantum yield of DNA in solution," *Zhurnal Prikladnoi Spektroskipii*, 1966, 5(5), 621-624.
Place et al., "Stabilization of the Aggregation of Cyanine Dyes at the Molecular and Nanoscopic Level," *Langmuir*, 2000, 16(23), 9042-9048.
Pschirer et al., "Poly(fluorenyleneethynylene)s by Alkyne Metathesis: Optical Properties and Aggregation Behavior," *Macromolecules*, 2000, 33(11), 3961-3963.
Rendina et al., "Oxidative Addition Reactions of Organplatinum (II) Complexes with Nitrogen-Donor Ligands," *J. Chem. Rev.*, 1997, 97(6), 1735-1754.
Rininsland et al., "High-Throughput Kinase Assays with Protein Substrates Using Fluorescent Polymer Superquenching," *MBC Biotech.*, 2005, 5(16), 1-6.
Rininsland et al., "Metal Ion-Mediated Polymer Superquenching for Highly Sensitive Detection of Kinase and Phosphatase Activities," *PNAS*, 2004, 101(43), 15295-15300.
Sandrini et al., "Photochemistry of the Orthometalated cis-Bis[2-(2-thienyl)pyridine]platinum(II) Complex in Halocarbon Solvents," *J. Am. Chem. Soc.*, 1987, 109(25), 7720.
Snow et al., "Synthesis and Evaluation of Hexafluorodimethylcarbinol Functionalized Polymers as Microsensor Coatings," *Journal of Applied Polymer Science*, 1991, 43, 1659-1671.
Swager et al., "Fluorescence Studies of Poly(*p*-phenyleneethynylene)s: The Effect of Anthracene Substitution," *J. Phys.Chem.*, 1995, 99(14), 4886-4893.
Swager, "The Molecular Wire Approach to Sensory Signal Amplification," *Acc. Chem. Res.*, 1998, 31(5), 201-207.
Tan et al., "Photophysics, aggregation and amplified quenching of a water-soluble poly(phenylene ethynylene)," *Chem. Commun.*, 2002, 446-447.
Thomas, III et al., "Amplifying fluorescent polymer sensors for the explosives taggant 2,3-dimethyl-2,3-dinitrobutane (DMNB)," *Chem. Commun.*, 2005, 4572-4574.
Thomas, III et al., "Conjugated Polymer Sensors: Design Principles Towards Enhanced Versatility," presented at the Army Science Conference, Dec. 2004.
Thomas, III et al., "Conjugated Polymer Sensors: Detection of DMNB and Hydrazine," presented at the Materials Research Symposium, Boston, MA, (Dec. 2005).
Thomas, III et al., "Conjugated Polymer Sensors: Detection of DMNB and Hydrazine," presented to the American Chemical Society, at the 230th National Meeting, Washington, D.C., (Aug. 28-Sep. 1, 2005).
Thomas, III et al., "Synthesis and Optical Properties of Simple Amine-Containing Conjugated Polymers," *Macromolecules*, 2005, 38(7), 2716-2721.
Thomas, III et al., "Trace Hydrazine Detection with Fluorescent Conjugated Polymers: A Turn-On Sensory Mechanism," *Adv. Materials*, 2006, 18, 1047-1050.
Thomas, III et al., "Designing Amplifying Polymer Sensors for Explosives and Toxic Chemicals," *Polymeric Materials: Science and Engineering*, 2006, 95, 81-82.
Thomas, III et al., "Dark-Field Oxidative Addition-Based Chemosensing: New Bis-cyclometalated Pt(II) Complexes and Phosphorescent Detection of Cyanogen Halides," *J. Am. Chem. Soc.*, 2006, 128, 16641-16648.
Toal et al., "Polymer sensors for nitroaromatic explosives detection," *Journal of Materials Chemistry*, 2006, 16, 2871-2883.
Van Houten et al., "Rapid Luminescent Detection of Phosphate Esters in Solution and the Gas Phase Using (dppe)Pt{S2C2(2-pyridyl)(CH2CH2OH)}," *J. Am. Chem. Soc.*, 1998, 120(47), 12359-12360.

Walters et al., "Photophysical Consequences of Conformation and Aggregation in Dilute Solutions of π-Conjugated Oligomers," *Langmuir*, 1999, 15(17), 5676-5680.
Waluk, "Hydrogen-Bonding-Induced Phenomena in Bifunctional Heteroazaaromatics," *Acc. Chem. Res.*, 2003, 36(11), 832-838.
Wang et al., "Biosensors from Conjugated Polyelectrolyte Complexes," *PNAS*, 2002, 99(1), 49-53.
Wang et al., "Fluorescein Provides a Resonance Gate for FRET from Conjugated Polymers to DNA Intercalated Dyes," *J. Am. Chem. Soc.*, 2004, 126(17), 5446-5451.
Wang et al., "Photoluminescence of Water-Soluble Conjugated Polymers: Origin of Enhanced Quenching by Charge Transfer," *Macromolecules*, 2000, 33(14), 5153-5158.
Wang et al., "Photoluminescence Quenching of Conjugated Macromolecules by Bipyridinium Derivatives in Aqueous Media: Charge Dependence," *Langmuir*, 2001, 17(4), 1262-1266.
Weder et al., "Efficient Solid-State Photoluminescence in New Poly(2,5-dialkoxy-*p*-phenyleneethynylene)s," *Macromolecules*, 1996, 29(15), 5157-5165.
Whitten et al., "From Superquenching to Biodetection: Building Sensors Based on Fluorescent Polyelectrolytes," Chapter 4, *Optical Sensors and Switches*, New York: Marcel Dekker, 2001, 189-208.
Willis et al., "Fluoresence decay kinetics of single tyrosinate and tyrosine hydrogen-bonded complexes," *J. Physical Chemistry*, 1991, 95(4), 1585-1589.
Wolfbeis, "Materials for fluorescence-based optical chemical sensors," *J. Mater. Chem.*, 2005, 15, 2657-2669.
Wosnick et al., "Layer-by-Layer Poly(phenylene ethynylene) Films on Silica Microspheres for Enhanced Sensory Amplification," *Macromolecules*, 2005, 38(22), 9287-9290.
Wosnick et al., "Synthesis and Application of Poly(phenylene Ethynylene)s for Bioconjugation: A Conjugated Polymer-Based Fluorogenic Probe for Proteases," *J. Am. Chem. Soc.*, 2005, 127(10), 3400-3405.
Wu et al., "Novel Nanoparticles Formed via Self-Assembly of Poly-(ethylene glycol-*b*-sebacic anhydride) and Their Degradation in Water," *Macromolecules*, 2000, 33(24), 9040-9043.
Wu et al., "Preparation and Encapsulation of Highly Fluorescent Conjugated Polymer Nanoparticles," *Langmuir*, 2006, 22(7), 2956-2960.
Xia et al., "A High-Throughput Screening Assay for Kinases and Phosphatases via Metal Ion-Mediated Fluorescent Polymer Superquenching," *American Laboratory*, 2004, 36, 15-19.
Xia et al., "Applications of Fluorescent Polymer Superquenching to High Throughput Screening Assays for Protein Kinases," *Assay and Drug Dev. Tech.*, 2004, 2(2), 183-192.
Yang et al., "Anomalous crystal packing of iptycene secondary diamides leading to novel chain and channel networks," *Tetrahedron Letters*, 2000, 41(41), 7911-7915.
Yang et al., "Fluorescent Porous Polymer Films as TNT Chemosensors: Electronic and Structural Effects," *J. Am. Chem. Soc.*, 1998, 120(46), 11864-11873.
Yang, et al., "Porous Shape Persistent Fluorescent Polymer Films: An Approach to TNT Sensory Materials," *J. Am. Chem. Soc.*, 1998, 120(21), 5321-5322.
Zhang et al., "Fluorescent Detection of Chemical Warfare Agents: Specific Ratiometric Chemosensors," *J. Am. Chem. Soc.*, 2003, 125, 3420-34231.
Zhang et al., "Formation of Novel Polymeric Nanoparticles," *Accounts of Chemical Research*, 2001, 34(3), 249-256.
Zhao et al., "Sensory Responses in Solution vs Solid State: A Fluorescence Quenching Study of Poly(iptycenebutadiynylene)s," *Macromolecules*, 2005, 38(22), 9377-9384.
Zhou et al., "Fluorescent Chemosensors Based on Energy Migration in Conjugated Polymers: The Molecular Wire Approach to Increased Sensitivity," *J. Am. Chem. Soc.*, 1995, 117(50), 12593-12602.
Zhou et al., "Methodology for Enhancing the Sensitivity of Fluorescent Chemosensors: Energy Migration in Conjugated Polymers," *Journal of the American Chemical Society*, 1995, 117(26), 7017-7018.
Chemical Structure for Biphenylene. CAS No. 259-79-0.
Institute for Soldier Nanotechnologies, (http://web.mit.edu/isn/industryday/index.html).

(56) References Cited

OTHER PUBLICATIONS

International Preliminary Report on Patentability dated Nov. 10, 2008 in PCT/US2007/017380.
International Search Report and Written Opinion dated Apr. 8, 2008 in PCT/US2007/017380.
International Search Report and Written Opinion dated Dec. 14, 2007 in PCT/US2007/020961.
International Preliminary Report on Patentability dated Apr. 28, 2009 in PCT/US2007/022670.
International Search Report and Written Opinion dated Oct. 27, 2008 in PCT/US2007/022670.
International Search Report and Written Opinion dated Jun. 13, 2008 in PCT/US2007/021370.
Thomas III, et al., "Molecules and Materials for the Optical Detection of Explosives and Toxic Chemicals," Dissertation, Massachusetts Institute of Technology, Jun. 2006.
Thomas III, et al., "Towards chemosensing phosphorescent conjugated polymers: cyclometalated platinum(II) poly(phenylene)s," J. Mater. Chem. 2005, 2829-2835.

* cited by examiner a.)

b.)

c.)

MV$^{+2}$    MV$^{+2}$-nap a.) b.)

EMISSIVE COMPOSITIONS WITH INTERNAL STANDARD AND RELATED TECHNIQUES

STATEMENT REGARDING FEDERALLY SPONSORED RESEARCH OR DEVELOPMENT

This invention was made with the support under the following government contract: DAAD19-02-D-002 awarded by the Army Research Office Institute for Soldier Nanotechnologies. The government has certain rights in the invention.

RELATED APPLICATIONS

This application claims priority under 35 U.S.C. §119(e) to U.S. Provisional Application Ser. No. 60/849,547, filed Oct. 5, 2006, the contents of which are incorporated herein by reference.

FIELD OF THE INVENTION

The present invention relates to materials, devices, and methods related to determination of analytes.

BACKGROUND OF THE INVENTION

Sensory devices based on amplified fluorescence quenching of solid-state conjugated polymer films can be highly sensitive, due to the amplification that arises from delocalized excitons sampling many potential binding sites within one excited state lifetime. Previous work has demonstrated highly sensitive detection schemes using these amplifying fluorescent polymers for a number of analytes in solution and vapor phase, as described in U.S. Publication No. 2003/0178607. In many cases, the transduction mechanism is photoinduced charge transfer (PICT) from a polymer donor to an analyte that binds via a tight pi-complex to the conjugated polymer.

In the detection of biological molecules, the sample may often contain various biological species in a complex, aqueous environment. Many conjugated polymers have been shown to exhibit nonspecific interactions with such species via, for example, electrostatic interactions, making it difficult to design a sensor that selectively interacts with a particular biological analyte of interest, such a protein.

Accordingly, improved methods are needed.

SUMMARY OF THE INVENTION

The present invention relates to particles comprising a core, an outer layer at least partially encapsulating the core, wherein the outer layer comprises a polymer material having a first emission upon exposure to a set of conditions, and a species having a second emission upon exposure to said set of conditions, wherein the species is integrally connected to at least a portion of the particle.

The present invention also relates to particles comprising a core, an outer layer at least partially encapsulating the core, wherein the outer layer comprises a polymer material having an emission, and a support material integrally connected to at least a portion of the particle such that the particle is substantially contained within the support material.

The present invention also relates to particles comprising a polymer material having a first emission upon exposure to a set of conditions and a species having a second emission upon exposure to said set of conditions, wherein a characteristic of the first emission is affected by an analyte for determination by the particle, and the second emission is essentially unaffected by the analyte.

The present invention also relates to sensors comprising a particle comprising a core comprising a polymeric material and an outer layer at least partially encapsulating the core, wherein the outer layer comprises an emissive polymer material, a source of energy applicable to the particle to cause an emission of radiation, and an emission detector positioned to detect the emission.

The present invention also provides methods for determination of an analyte comprising providing a particle having an emission, wherein the particle comprises a core and an outer layer at least partially encapsulating the core, wherein the outer layer comprises an emissive polymer material; exposing the particle to a sample suspected of containing an analyte wherein the analyte, if present, interacts with the particle to produce a change in the emission of the particle; and determining the change in the emission of the particle, thereby determining the analyte.

The present invention also provides methods for quantitative determination of the concentration of an analyte comprising providing a particle comprising a polymer material and a species, wherein, upon exposure to a set of conditions, the polymer material has a first emission and the species has a second emission, wherein the maximum of the first emission and the maximum of the second emission are separated by at least 50 nm; determining a first ratio between a characteristic of the first emission and a characteristic of the second emission; exposing the particle to an analyte, wherein the analyte interacts with the polymer material to produce a third emission; determining, upon exposure to said set of conditions, a second ratio between a characteristic of the second emission and a characteristic of the third emission, wherein the second ratio is different than the first ratio; and determining the difference between the first ratio and the second ratio, thereby quantitatively determining the concentration of the analyte.

DETAILED DESCRIPTION

Figure 1A:
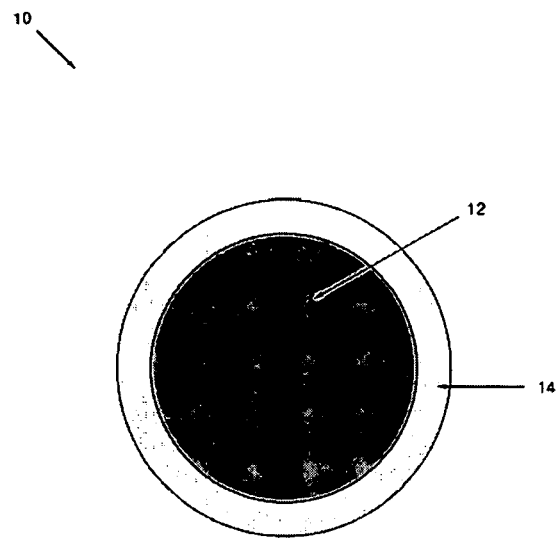
FIG. 1A shows a schematic representation of a particle having a core and an outer layer, according to one embodiment of the invention.

The present invention generally relates to emissive particles and related methods, including determination of an analyte.

In some cases, the present invention provides materials (e.g., particles), devices (e.g., sensors), and methods related to determination of an analyte. The analytes may be determined by monitoring, for example, a change in an optical signal of a luminescent material upon exposure to an analyte. In some cases, the present invention may be used for the detection of analytes such as biological molecules (e.g., proteins, and the like). Methods of the invention may also be useful in the quantitative determination of an analyte.

The present invention may be particularly advantageous in that some embodiments may comprise an emissive species useful as an internal reference standard. For example, the present invention may comprise materials (e.g., particles) which contain a first emissive species that may be utilized in the determination of an analyte and a second emissive species that may be employed as an internal reference standard. The emission of the first emissive species may have a characteristic which, upon exposure to an analyte, may be affected (e.g., altered) by an analyte, while the emission of the second emissive species may be essentially unaffected by the analyte. The emission of the second emissive species may then be compared to the emission of the first emissive species to observe the change in the first emissive species upon exposure to an analyte. For example, the present invention may provide particles comprising a polymer material having a first emission upon exposure to a set of conditions (e.g., electromagnetic radiation) and a species having a second emission upon exposure to said set of conditions, wherein the species is useful as an internal reference standard. The internal reference standard may allow for both precise measurement of a signal and quantification of an analyte.

The present invention may also be advantageous for determination of analytes in samples, such as biological or biochemical samples, wherein nonspecific interaction between analytes and the sensing element(s) of a sensor might otherwise occur. In some cases, materials, sensors, and methods of the invention may allow for selective interaction with a particular analyte in the presence of other species, thereby allowing for selective determination of an analyte. For example, materials (e.g., particles) of the invention may be exposed to an aqueous, biological sample comprising various species, including cells, proteins, small molecules, and the like, wherein the material may specifically interact with a particular analyte. In some cases, materials and devices of the invention may be constructed and arranged such that a specific interaction with an analyte may occur, as described more fully below. In some embodiments, the sensing elements (e.g., particles) may be dispersed throughout a support material, wherein the support material may be designed to selectively allow interaction between the particles and specific analytes based on, for example, the size of the analyte.

In some embodiments, the present invention provides particles for use as a sensing element. The particles may comprise a core and an outer layer at least partially encapsulating the core, wherein the outer layer may comprise a polymer material having a first emission upon exposure to a set of conditions. As shown in FIG. 1A, particle 10 comprises a core 12 and an outer layer 14, which surrounds core 12. In some cases, the outer layer completely encapsulates the core. The outer layer may comprise an inorganic material, an organic material, or combinations thereof. In some cases, the outer layer comprises a polymer material, such as an emissive or luminescent polymer material, which may be capable of interacting with an analyte. The emissive polymer material may interact with the analyte via, for example, a charge transfer reaction or formation of a bond.

In some embodiments, the particle may further comprise a species having an emission, wherein the emission is different from the emission of the outer layer. That is, in some cases, the polymer material has a first emission and the species has a second emission upon exposure to the same set of conditions (e.g., exposure to electromagnetic radiation). For example, in some cases, the invention may comprise the use of a particle comprising both a polymer material and a species contained within the same particle such that exposure of the particle to a set of conditions allows both the polymer material and the species to be exposed an essentially identical set of conditions at the same time. As used herein, exposure to a "set of conditions" may comprise, for example, exposure to a particular temperature, pH, solvent, chemical reagent, type of atmosphere (e.g., nitrogen, argon, oxygen, etc.), electromagnetic radiation, or the like. In some embodiments, a particle comprising a polymer material and a species may be exposed to electromagnetic radiation having a particular wavelength (e.g., excitation energy), wherein the polymer material produces a first emission and the species produces a second emission, wherein the first emission and the second emission occur at different wavelengths. In some cases, the maximum of the first emission is separated from the maximum of the second emission by at least 100 nm, or, in another embodiment, by at least 125 nm, or by at least 150 nm. In some cases, particles comprising the species may be useful in determination of an analyte, such as quantitative determination of an analyte, as described more fully below.

In some embodiments, a characteristic of the first emission may be affected by an analyte for determination by the particle, while the second emission may be essentially unaffected by the analyte. For example, a characteristic of the particle may be "affected by an analyte" such that an interaction between the particle, or portion thereof, and the analyte results in a measurable change of the characteristic. In some embodiments, the luminescence intensity of the first emission (e.g., the emission of the outer layer) is affected by the analyte. In some cases, a characteristic of a particle may be "essentially unaffected" by an analyte, if, in the presence of the analyte, the characteristic of the particle changes by less than 10%, or, in some embodiments, less than 5%, less than 1%, or less than 0.5%. For example, the particle may comprise a species having an emission in the absence of analyte, wherein the emission has a luminescence intensity and occurs at a particular wavelength. Upon exposure to an analyte, the luminescence intensity and/or wavelength of the species may change by less than 10%, thereby remaining "essentially unaffected" by the analyte. This may allow the species to be useful as an internal reference standard.

Figure 8:
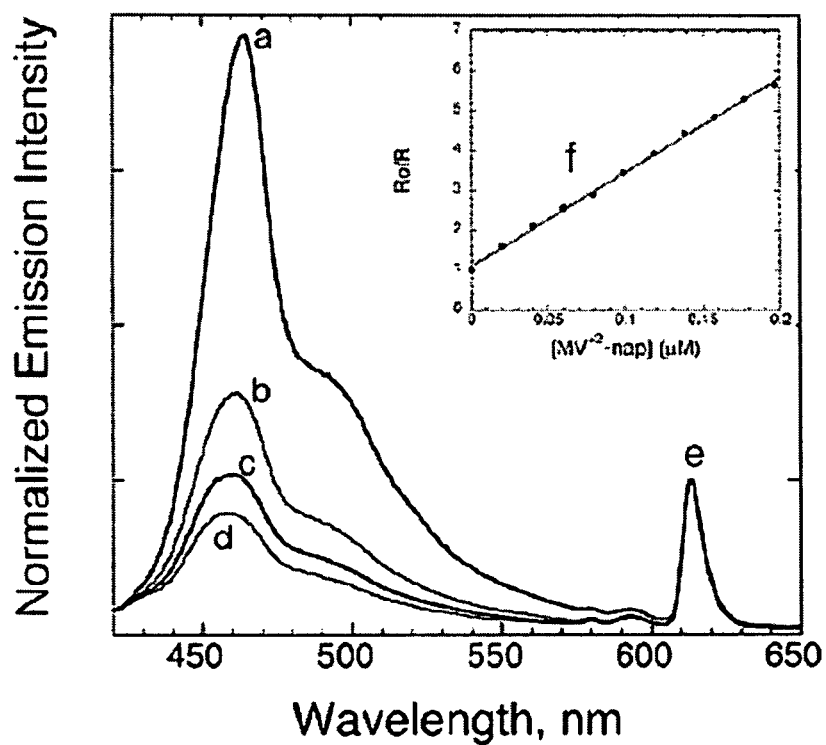
FIG. 8 shows the response of P1-coated particles in Tris buffer (20 mM, pH 7.4) towards $MV^{2+}$-nap, with Eu as reference at 612 nm, in response to the addition of (a) 0.00 µM, (b) 0.06 µM, (c) 0.12 µM, and (d) 0.18 µM of $MV^{2+}$-nap, as well as (e) the Eu reference peak and (f) the Stem-Volmer plot of $R_0/R$ vs. [$MV^{2+}$-nap] with linear best fit.

In an illustrative embodiment, FIG. 8 shows the fluorescence emission spectra of a particle comprising an emissive polymer material having an emission around 465 nm and a plurality of europium atoms having an emission around 615 nm, upon exposure to the same electromagnetic radiation. Upon exposure to increasing amounts of a quenching molecule, the emissive polymer material interacts with the quenching molecule and a decrease in luminescence intensity at around 465 nm is observed. By contrast, the quenching molecule does not interact with the plurality of europium atoms, and the emission at around 615 nm remains substantially unchanged.

In some embodiments, the species may be integrally connected to at least a portion of the particle. As used herein, the term "integrally connected," when referring to two or more objects, means objects that do not become separated from each other during the course of normal use, e.g., separation requires at least the use of tools, and/or by causing damage to at least one of the components, for example, by breaking, peeling, dissolving, etc. In some embodiments, the species may be dispersed throughout a portion of the particle, such as the core, the outer layer, or both. In one embodiment, the species is dispersed throughout the core. The species may be any emissive species that does not interact with the analyte and/or does not affect or interfere with the interaction between the analyte and the outer layer of the particle. In some cases, the species is a metal species, such as europium or platinum, or a dye molecule. In one embodiment, the species is europium. In one particular embodiment, particles comprises a core comprising polystyrene and a plurality of europium atoms dispersed throughout the core.

Figure 1B:
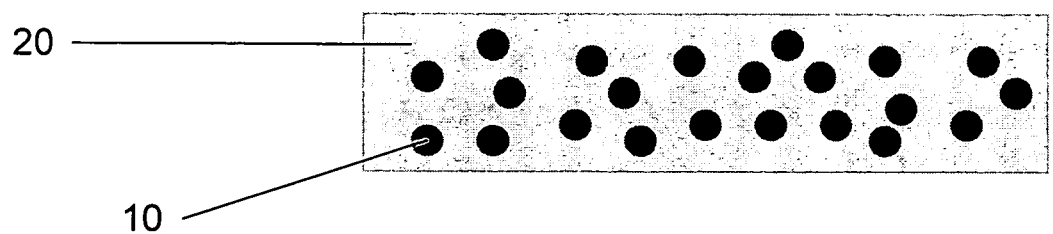
FIG. 1B shows a schematic representation of a plurality of particles contained within a support material, according to one embodiment of the invention.

In some embodiments, particles of the invention may also further comprise a support material. For example, in some embodiments, particles of the invention may comprise a core, an outer layer at least partially encapsulating the core, wherein the outer layer comprises a polymer material having an emission, and a support material that may be integrally connected to at least a portion of the particle. In some cases, the particle or plurality of particles may be substantially contained within the support material. As shown in FIG. 1B, particles 10 are dispersed within a support material 20, such that the particles are substantially contained within support material 20. The particle(s) may optionally comprise an emissive species that may be useful as an internal reference standard, as described herein.

The support material may be designed to facilitate selective diffusion of an analyte through the support material, such that the analyte may interact with the particle or particles dispersed within the support material and other species present in the sample may be prevented from interacting with the particles. For example, the support material may be a porous material, wherein the size of the pores may be selected to allow the diffusion of small analytes while preventing the diffusion of larger analytes. In some embodiments, the support material may be a polymer, such as a hydrogel. In some embodiments, the support material may be a semi-permeable membrane. In some embodiments, the support material may be compatible with aqueous environments. Other properties of the support material such as hydrophobicity, hydrophilicity, swellability, degree of crosslinking, and the like, may also be selected to suit a particular application.

The present invention also provides sensors comprising particles as described herein. For example, the sensor may comprise a particle comprising a core comprising a polymeric material and an outer layer at least partially encapsulating the core, wherein the outer layer comprises an emissive polymer material. The particle may further comprise an emissive species (e.g., internal reference standard) or a support material, as described herein. The sensor may also further comprise a source of energy applicable to the particle to cause an emission of radiation and an emission detector positioned to detect the emission. In some cases, the sensor may comprise a plurality of particles. The plurality of particles may be suspended in solution, or, in some cases, the particles may be dispersed throughout a support material.

Particles comprising a core-shell or core-outer layer configuration are described herein by way of example only, and it should be understood that, in some cases, other configurations of particles and particle components may be encompassed within the scope of the invention. For example, the particle may comprise an emissive polymer material and another, emissive species evenly dispersed throughout the particle, wherein the emissive polymer material may be useful as a sensing element and the other, emissive species may be useful as an internal reference standard.

Methods for determination of an analyte may comprise providing a particle having an emission, as described herein, and exposing the particle to a sample suspected of containing an analyte wherein the analyte, if present, interacts with the particle to produce a change in the emission of the particle. For example, the analyte may interact with the outer layer of the particle. The change in the emission of the particle may then be determined, thereby determining the analyte. In some cases, the change comprises a decrease in luminescence intensity. In some cases, the change comprises an increase in luminescence intensity. In some cases, the change comprises a change in the wavelength of the luminescence, either alone or in combination with a change in the luminescence intensity of the emission. In some embodiments, change may be caused by a photoinduced charge transfer reaction between the emissive polymer material and the analyte.

The sensor may further comprise a support material, as described herein, wherein the support material may facilitate the selective permeation or diffusion of an analyte. For example, the support material may be a semi-permeable membrane wherein selective diffusion or permeation of an analyte allows determination of the analyte in the presence of other species. In some cases, the analyte may permeate the support material and directly interact with particles of the invention. Alternatively, in some cases, sensors and methods of the invention may determine an analyte by determining a molecule that may be selectively generated or selectively released by the analyte. The generated or released molecule may then interact with the particles as described herein, causing a change in the emission of the particles.

Figure 1C:
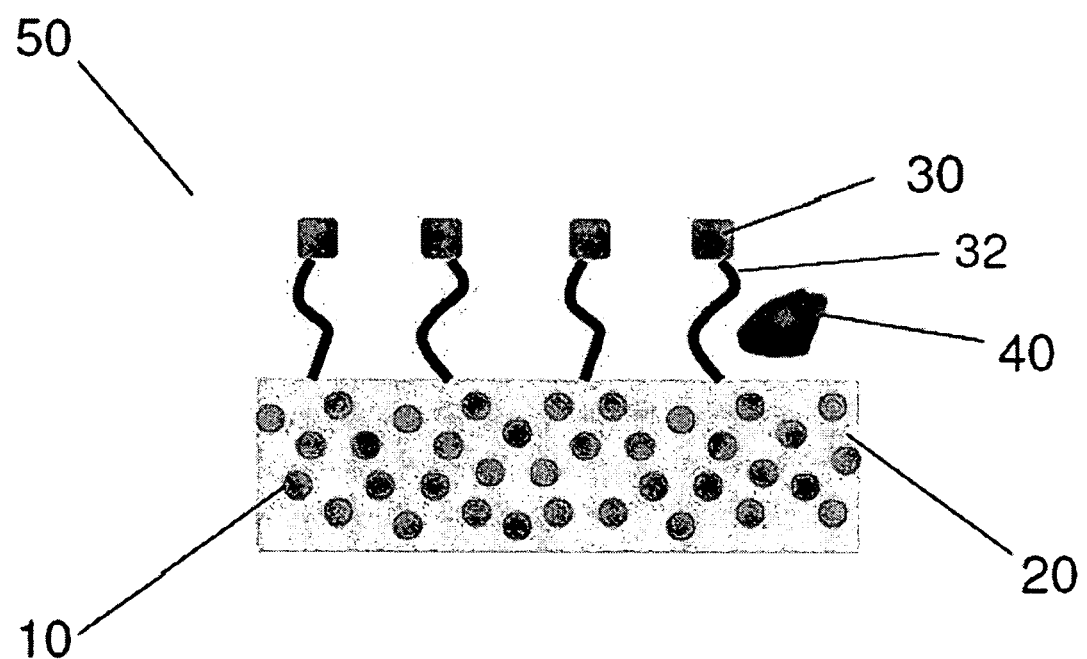
FIG. 1C shows a schematic representation of a particle-containing hydrogel and transduction scheme to detect biological events.

In the illustrative embodiment shown in FIG. 1C, sensor 50 comprises a plurality of particles 10 dispersed within support material 20, wherein the particles 10 have an emission. Support material 20 may be selected such that analyte 40 may not readily diffuse through the support material, for example, due to size exclusion. Sensor 50 may further comprise a small, quenching molecule 30 attached to the surface of the support material 20 via a linker 32 such that quenching molecule 30 does not contact particles 10 dispersed within support material 20. In the presence of analyte 40, linker 32 may be selectively cleaved such that quenching molecule 30 is released from the surface of support material 20. For example, the analyte may be a protein and the linker may be a peptide that is selectively cleaved by the protein. Quenching molecule 30 may be appropriately sized such that it may then diffuse through support material 20 to interact with particles 10, causing a change in the emission of the particles, thereby signalling the presence of analyte 40.

In one embodiment, the quenching molecule is methyl viologen or a derivative thereof, and the linker is a peptide that is selectively cleaved by a particular protein. The linker may be bonded to the quenching molecule and the support material via a covalent bond, ionic bond, dative bond, or the like. The peptide linker may be selected to interact with a particular protein, such that, in the presence of the protein, the peptide linker may be cleaved by the protein, thus releasing the quenching molecule, which may then diffuse into the support material to interact with particles of the invention. The attachment of a quenching molecule is described herein by way of example only, and it should be understood that other moieties that may facilitate the determination of an analyte may be attached to the surface of the support material. Similarly, the use of a peptide linker is described herein by way of example only, and it should be understood that other linkers that may be selectively cleaved or otherwise altered by an analyte may also be attached to the surface of the support material.

Such methods may be useful in the determination of, for example, an amount or concentration of a particular analyte. The inclusion of an internal reference standard may, in some cases, allow for the quantitative determination of an analyte. For example, a method may comprise providing a particle comprising a polymer material and a species (e.g., an internal reference standard). Upon exposure to a set of conditions, the polymer material may have a first emission and the species may have a second emission, wherein the first emission and the second emission are separated by at least 50 nm, and a first ratio between a characteristic of the first emission and a characteristic of the second emission may be determined. For example, the characteristic may be luminescence intensity, wavelength of emission, or the like. The particle may then be exposed to an analyte, wherein the analyte may interact with at least a portion of the particle (e.g., the outer layer of the particle) to produce a third emission, and, upon exposure to said set of conditions, a second ratio between a characteristic of the second emission and a characteristic of the third emission may be determined, wherein the second ratio is different than the first ratio. Determination of the difference between the first ratio and the second ratio may thereby quantitatively determine the concentration of the analyte.

In some cases, the first ratio may be a ratio between the luminescence intensity of the first emission and the luminescence intensity of the second emission, and the second ratio may be a ratio between the luminescence intensity of the second emission and the luminescence intensity of the third emission. In some cases, the luminescence intensity of the third emission may be decreased relative to the luminescence intensity of the first emission. In some cases, the luminescence intensity of the third emission may be increased relative to the luminescence intensity of the first emission. In some cases, the wavelength of the third emission may be shifted relative to the wavelength of the first emission.

In some cases, the interaction between the particle and the analyte may comprise, for example, energy transfer (e.g., photoinduced charge transfer, fluorescence resonance energy transfer), electrostatic interactions, binding interactions, redox reactions (e.g., reduction, oxidation), other chemical reactions, and the like. In some cases, the analyte may be an electron acceptor and the particle, or portion thereof, may be an electron donor. In some cases, the analyte may be an electron donor and the particle, or portion thereof, may be an electron acceptor.

In some embodiments, the interaction between the particle and the analyte may comprise an interaction between the emissive polymer material (e.g., luminescent polymer) and the analyte. The interaction may comprise photoinduced charge transfer, wherein an excited-state polymer transfers an electron to an analyte. For example, an emissive polymer material may form an excited state upon exposure to electromagnetic radiation and produce a first emission signal. In the excited-state, the emissive polymer material may then interact with (e.g., transfer charge to) an analyte, resulting in a second emission which has decreased or "quenched" luminescence intensity (e.g., a "turn-off" detection mechanism). Alternatively, the interaction between the emissive polymer material and the analyte may comprise a chemical reaction which may increase the luminescence intensity of the polymer. The emissive polymer material may exist in a "quenched" state and have substantially no emission signal upon exposure to electromagnetic radiation, wherein, upon interaction with an analyte, the analyte may interact with at least a portion of the emissive polymer material and/or a quenching molecule associated with the emissive polymer material such that an emission signal is generated that has a greater luminescence intensity than the emission signal in the absence of analyte upon exposure to the same conditions of electromagnetic radiation (e.g., a "turn-on" detection mechanism).

In some cases, methods of the invention comprise determining a change in the wavelength of an emission signal. The wavelength of an emission signal refers to the wavelength at which the peak maximum of the emission signal occurs in an emission spectrum. The emission signal may be a particular peak having the largest intensity in an emission spectrum (e.g. a fluorescence spectrum), or, alternatively, the emission signal may be a peak in an emission spectrum that has at least a defined maximum, but has a smaller intensity relative to other peaks in the emission spectrum.

In some embodiments, the change in luminescence intensity may occur for an emission signal with substantially no shift in the wavelength of the luminescence (e.g., emission), wherein the intensity of the emission signal changes but the wavelength remains essentially unchanged. In other embodiments, the change in luminescence intensity may occur for an emission signal in combination with a shift in the wavelength of the luminescence (e.g., emission). For example, an emission signal may simultaneously undergo a shift in wavelength in addition to an increase or decrease in luminescence intensity. In another embodiment, the change may comprise two emission signals occurring at two different wavelengths, wherein each of the two emission signals undergoes a change in luminescence intensity. In some cases, the two emission signals may undergo changes in luminescence intensity independent of one another. In some cases, the two emission signals may undergo changes in luminescence intensity, wherein the two emission signals are associated with one another, for example, via an energy transfer mechanism, as described more fully below.

In some embodiments, methods of the present invention may further comprise determining a change in the wavelength of the luminescence upon exposure of a particle as described herein to an analyte. That is, in some cases, determination of an analyte may comprise observing a change in luminescence intensity in combination with a change in the luminescence wavelength. For example, the relative luminescence intensities of a first emission signal and a second emission signal associated with the first emission signal may be modulated using the quenching and unquenching methods described herein. In some cases, the first emission signal and the second emission signal may be associated with (e.g., interact with) one another via an energy transfer mechanism, such as fluorescence resonance energy transfer, for example. The term "fluorescence resonance energy transfer" or "FRET" is known in the art and refers to the transfer of excitation energy from an excited state species (i.e., FRET donor) to an acceptor species (i.e., FRET acceptor), wherein an emission is observed from the acceptor species. In some cases, the FRET donor may be a luminescent polymer, portion(s) thereof, or other species, such as an analyte. Similarly, the FRET acceptor may be a luminescent polymer, portion(s) thereof, or other species, such as an analyte.

In one embodiment, a first portion of a luminescent polymer may act as FRET donor and a second portion within the same luminescent polymer may act as a FRET acceptor, wherein the first portion and the second portion each have different emission wavelengths. The luminescent polymer may be associated with a quenching molecule and exist in a "quenched" state, wherein, upon exposure of the first portion to electromagnetic radiation, the quenching molecule absorbs the excitation energy and substantially no emission is observed. Upon exposure to an analyte, the analyte may interact with the luminescent polymer and/or quenching molecule to "un-quench" the luminescent polymer. As a result, exposure of the first portion to electromagnetic radiation produces an excited-state, wherein the first portion of the luminescent polymer may transfer excitation energy to the second portion of the luminescent polymer, and emission signal from the second portion is observed.

Particles of the invention may have any particle size or average particle size suitable for use in a particular application. As used herein, "particle size" refers to the largest characteristic dimension (e.g., diameter) that can be measured along any orientation of a particle. Particle size may be determined by, for example, dynamic light scattering. For example, the particle size may be in the range from about 0.001 and 10 microns, or 0.01 and 5.0 microns, or 0.01 and 3.0 microns, or 0.1 and 1.0 micron (e.g., 0.2 microns). In one embodiment, the average particle size may be 0.2 microns.

As described herein, some particles of the invention may comprise a core, wherein the core may be any material that is capable of forming a particle. In some cases, it may be preferred that the core be optically transparent. In some cases, the core may have an emission, such that the emission occurs at a sufficiently different wavelength to not interfere or affect the determination methods described herein. In some cases, the core comprises a polymeric material. Examples of polymeric materials suitable for use as a core include, but are not limited to, polystyrene, polyacrylate, poly(methyl methacrylate), polyethylene, polypropylene, poly(vinyl chloride), poly(vinyl benzoate), poly(vinyl acetate), polyacrylamide, poly(vinyl butyral), polyurethane, polyacetal, polycarbonate, polyester, polyether, polybutadiene, substituted derivatives thereof, or combinations thereof. In one embodiment, the core comprises polystyrene.

As described herein, the particle comprises an outer layer or shell that encapsulates, or partially encapsulates, a core. In some embodiments, it is preferable for the outer layer to encapsulate the majority of the surface area of the core. For example, the outer layer may encapsulate at least 50%, at least 75%, or at least 95% of the surface area of the core. In some cases, the outer layer may completely encapsulate the emissive core. In some embodiments, the outer layer is not chemically bound to the core and yet may contain the core by encapsulation. In some cases, the outer layer may comprise an organic material (e.g., based on carbon and/or polymers of carbon). In some cases, the outer layer may comprise a non-organic material (e.g., not based on carbon and/or polymers of carbon, but nonetheless may include carbon atom). It may be preferred for the outer layer to be an organic material, such as a luminescent polymer. In certain embodiments, the outer layer may be porous. For example, the outer layer may have pores on the mesoscale size. In certain embodiments, the outer layer may be non-porous.

Some embodiments of the invention comprise an outer layer comprising a luminescent polymer, such as a fluorescent polymer. For example, in some cases, the particle may be coated with an outer layer comprising a luminescent polymer. The luminescent polymer may comprise the structure,

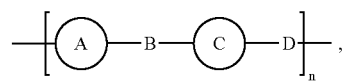

wherein n is at least 1, A and C are optionally substituted aromatic groups, and B and D are absent, alkene, alkyne, heteroalkene, or heteroalkyne. In other embodiments of the invention, poly(phenylene ethynylene)s may be used, wherein B and D are alkynes.

Figure 2:
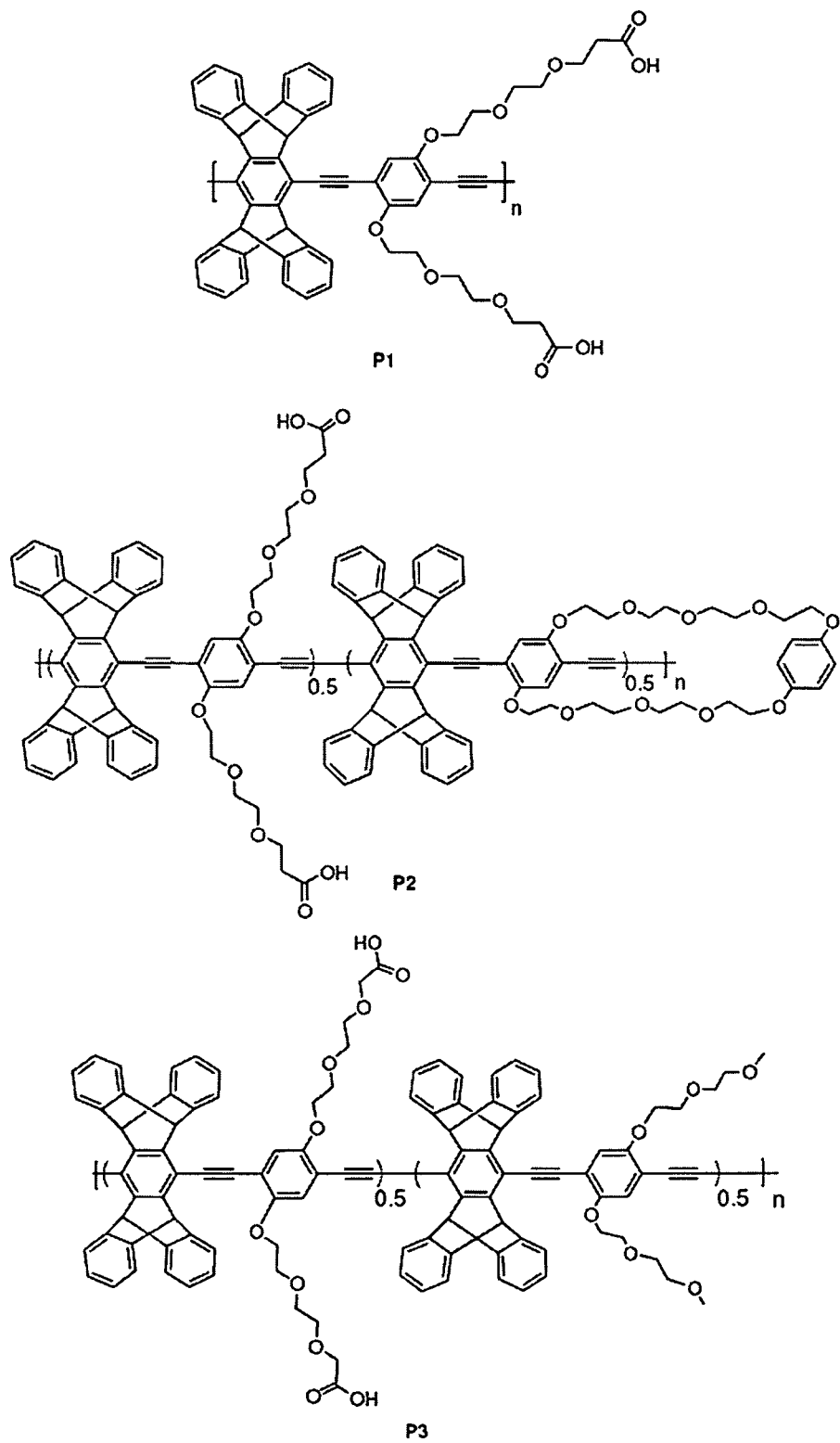
FIG. 2 shows the chemical structure of several luminescent polymers that may be coated onto microspheres, according to some embodiments of the invention.

In some cases, the luminescent polymer has the structure,

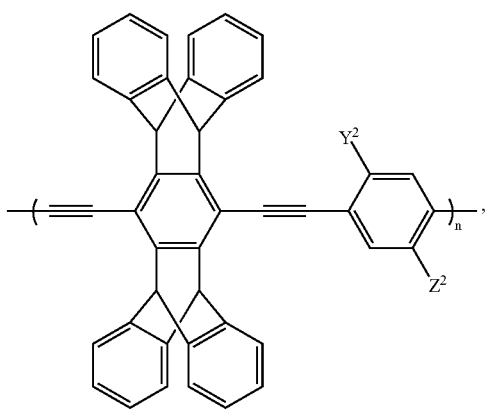

wherein $Y^2$ and $Z^2$ can be the same or different and can be alkyl, heteroalkyl, or substituted derivatives thereof. In some embodiments, $Y^2$ and $Z^2$ are joined together to form a ring. In one embodiment, $Y^2$ and $Z^2$ are heteroalkyl such as ethylene glycol chains. As used herein, an ethylene glycol chain is given its ordinary meaning in the art and refers to a heteroalkyl chain comprising the formula "$(CH_2O)_n$," which may be optionally substituted, wherein n is at least 1. In one embodiments, $Y^2$ and $Z^2$ are ethylene glycol chains substituted with a carboxylic acid group, such as a terminal carboxylic acid group. FIG. 2 shows some examples of such polymers (e.g., polymers P1-P3). It should be understood that polymers of the invention may be further substituted with additional functional groups, as described herein.

As used herein, an emitted radiation or "emission" may be luminescence emission, in which "luminescence" is defined as an emission of ultraviolet or visible radiation. Specific types of luminescence include fluorescence, in which a time interval between absorption and emission of visible radiation ranges from $10^{-12}$ to $10^{-7}$ s, phosphorescence, other types of luminescence, and the like. For example, the emission may be "chemiluminescence," which refers to emission of radiation due to a chemical reaction, or "electrochemiluminescence," which refers to emission of radiation due to electrochemical reactions. In some cases, the emission may be fluorescence emission.

As used herein, a "luminescent polymer" refers to a polymer that can absorb a quantum of electromagnetic radiation to cause the polymer to achieve an excited state structure. Luminescent polymers may also be capable of emitting radiation. Radiation can be emitted from the polymer or from a chromophore associated with (e.g., covalently bound to, non-covalently bound to, etc.) the polymer. Typically, the extent of delocalized bonding allows the existence of a number of accessible electronic excited states. If the conjugation is so extensive so as to produce a near continuum of excited states, electronic excitations can involve a valence band, the highest fully occupied band, and a conduction band, often referred to as a band gap, as described herein.

Luminescent polymers may be used in various detection schemes for the determination of analytes. In some cases, the luminescent polymer may be used in a "turn-off" detection mechanism, wherein, in the presence of analyte, the excited state of a luminescent polymer interacts with the analyte via photoinduced electron transfer to "quench" the luminescence (e.g., fluorescence, phosphorescence, etc.) of the polymer. "Quenching" of luminescence may occur when a chromophore such as a luminescent polymer in an excited state is exposed to an "acceptor" species that can absorb energy from the excited state chromophore. The excited state chromophore returns to a ground state due to nonradiative processes (i.e. without emitting radiation), resulting in a reduced quantum yield. A "quantum yield" refers to a number of photons emitted per adsorbed photon. Thus, the excited state chromophore can function as a "donor" species in that it transfers energy to the acceptor species. The acceptor species can be an external molecule (e.g., analyte) or an internal species such as another portion of the same polymer. For example, a "turn-off" detection method may be used to determine the presence and/or amount of an analyte. Alternatively, the luminescent polymer may be used in a "turn-on" detection mechanism, wherein, in the absence of analyte, the luminescent polymer may exist in a quenched state and substantially no emission signal, or a significantly reduced emission signal, is observed. In the presence of analyte, the polymer may interact with the analyte to produce an emission. This process may be referred to as a "turn-on" luminescence detection method. For example, a "turn-on" detection method may be used to determine the presence and/or amount of hydrazine or derivatives of hydrazine, as described herein. In some cases, the "turn-on" fluorescence sensory scheme may be preferred since there are often fewer potential interferents that could cause a false positive with an emission increase or "turn-on" detection scheme.

Polymers, as used herein, refer to extended molecular structures comprising a backbone (e.g., non-conjugated backbone, conjugated backbone) which optionally contain pendant side groups, where "backbone" refers to the longest continuous bond pathway of the polymer. In one embodiment, at least a portion of the polymer is conjugated or pi-conjugated, i.e. the polymer has at least one portion along which electron density or electronic charge can be conducted, where the electronic charge is referred to as being "delocalized." Each p-orbital participating in conjugation can have sufficient overlap with adjacent conjugated p-orbitals. In one embodiment, at least a portion of the backbone is conjugated. In one embodiment, the entire backbone is conjugated and the polymer is referred to as a "conjugated polymer." Polymers having a conjugated pi-backbone capable of conducting electronic charge may be referred to as "conducting polymers." In some cases, the conjugated pi-backbone may be defined by a plane of atoms directly participating in the conjugation, wherein the plane arises from a preferred arrangement of the p-orbitals to maximize p-orbital overlap, thus maximizing conjugation and electronic conduction. In some cases, the pi-backbone may preferably have a non-planar or twisted ground state conformation, leading to decreased conjugation and a higher energy conduction band.

In one embodiment, the luminescent polymer is selected from the group consisting of polyarylenes, polyarylene vinylenes, polyarylene ethynylenes and ladder polymers, i.e. polymers having a backbone that can only be severed by breaking two bonds. Examples of such polymers include polythiophene, polypyrrole, polyacetylene, polyphenylene and substituted derivatives thereof.

Figure 3:
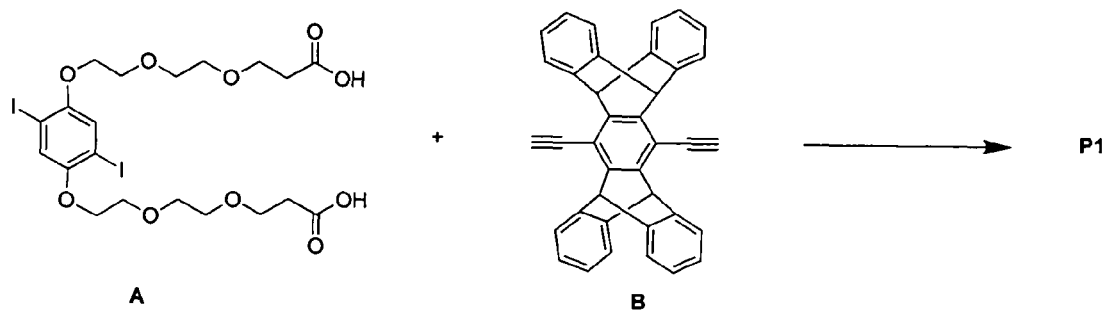
FIG. 3 shows illustrative embodiments of synthetic schemes for synthesizing (a) a carboxylic acid substituted poly(phenylene ethynylene), (b) a macrocycle-substituted poly(phenylene ethynylene), and (c) an ethylene glycol-substituted poly(phenylene ethynylene).
Figure 3:
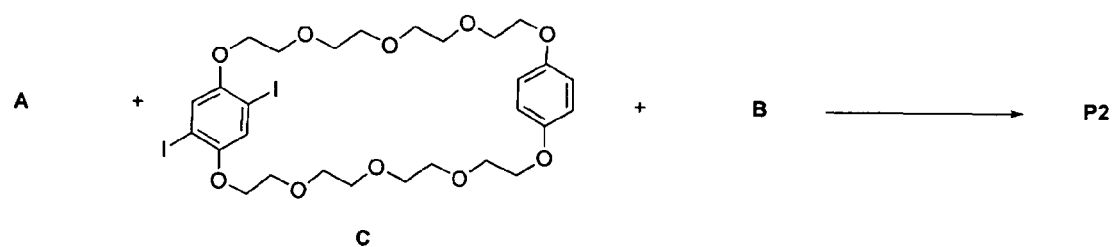
Figure 3:
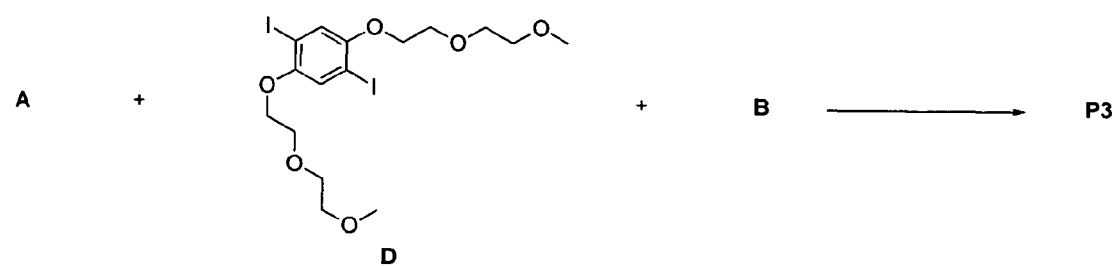

The luminescent polymers as described herein may by synthesized using known methods, such as those disclosed in Yang, et al., *J. Am. Chem. Soc.* 1998, 120, 12389; Thomas III, et al., *Macromolecules* 2005, 38, 2716; Morin, et al., *Macromolecules* 2001, 34, 4680, incorporated herein by reference. For example, FIGS. 3A-C show illustrative embodiments of synthetic schemes for synthesizing poly(phenylene ethynylene)s, wherein polymerization of a di-halide containing monomer and a di-acetylene-containing monomer via a metal-catalyzed Sonogashira cross-coupling reaction can produce the polymer. Poly(phenylene)s may be synthesized using known methods, such as those disclosed in Lamba, et al., *J. Am. Chem. Soc.* 1994, 116, 11723 and Bredas, et al., *Polym. Prepr. (Am. Chem. Sco., Div. Polym. Chem.)* 1994, 35, 185, incorporated herein by reference.

The properties of the luminescent polymers may also be tuned based on the substitution of the conjugated polymer backbone. Those skilled in the art would recognize what types of functional groups would afford a particular, desired property, such as the ability to determine an analyte. In one set of embodiments, luminescent polymers may be functionalized with a binding site for determination of a target analyte, wherein the luminescent polymer may be functionalized with a binding site capable of interacting with a target analyte. For example, a sample suspected of containing an analyte may be exposed to luminescent polymer as described herein. The analyte may interact with the luminescent polymer to cause a change in a property of the luminescent polymer, such as an optical property, wherein the change in the property may then determine the analyte. As used herein, the term "determination" or "determining" generally refers to the analysis of a species or signal, for example, quantitatively or qualitatively, and/or the detection of the presence or absence of the species or signals. "Determination" or "determining" may also refer to the analysis of an interaction between two or more species or signals, for example, quantitatively or qualitatively, and/or by detecting the presence or absence of the interaction.

In some embodiments, the interaction between the analyte and the binding site may comprise formation of a bond, such as a covalent bond (e.g. carbon-carbon, carbon-oxygen, oxygen-silicon, sulfur-sulfur, phosphorus-nitrogen, carbon-nitrogen, metal-oxygen or other covalent bonds), an ionic bond, a hydrogen bond (e.g., between hydroxyl, amine, carboxyl, thiol and/or similar functional groups, for example), a dative bond (e.g. complexation or chelation between metal ions and monodentate or multidentate ligands), or the like. The interaction may also comprise Van der Waals interactions. In one embodiment, the interaction comprises forming a covalent bond with an analyte. The binding site may also interact with an analyte via a binding event between pairs of biological molecules. For example, the polymeric structure may comprise an entity, such as biotin that specifically binds to a complementary entity, such as avidin or streptavidin, on a target analyte.

In some cases, the binding site may comprise a biological or a chemical molecule able to bind to another biological or chemical molecule in a medium (e.g., solution, vapor phase, solid phase). For example, the binding site may be a functional group, such as a thiol, aldehyde, ester, carboxylic acid, hydroxyl, or the like, wherein the functional group forms a bond with the analyte. In some cases, the binding site may be an electron-rich or electron-poor moiety within the polymer, wherein interaction between the analyte and the conducting polymer comprises an electrostatic interaction.

The binding site may also be capable of biologically binding an analyte via an interaction that occurs between pairs of biological molecules including proteins, nucleic acids, glycoproteins, carbohydrates, hormones, and the like. Specific examples include an antibody/peptide pair, an antibody/antigen pair, an antibody fragment/antigen pair, an antibody/antigen fragment pair, an antibody fragment/antigen fragment pair, an antibody/hapten pair, an enzyme/substrate pair, an enzyme/inhibitor pair, an enzyme/cofactor pair, a protein/substrate pair, a nucleic acid/nucleic acid pair, a protein/nucleic acid pair, a peptide/peptide pair, a protein/protein pair, a small molecule/protein pair, a glutathione/GST pair, an anti-GFP/GFP fusion protein pair, a Myc/Max pair, a maltose/maltose binding protein pair, a carbohydrate/protein pair, a carbohydrate derivative/protein pair, a metal binding tag/metal/chelate, a peptide tag/metal ion-metal chelate pair, a peptide/NTA pair, a lectin/carbohydrate pair, a receptor/hormone pair, a receptor/effector pair, a complementary nucleic acid/nucleic acid pair, a ligand/cell surface receptor pair, a virus/ligand pair, a Protein A/antibody pair, a Protein G/antibody pair, a Protein L/antibody pair, an Fc receptor/antibody pair, a biotin/avidin pair, a biotin/streptavidin pair, a drug/target pair, a zinc finger/nucleic acid pair, a small molecule/peptide pair, a small molecule/protein pair, a small molecule/target pair, a carbohydrate/protein pair such as maltose/MBP (maltose binding protein), a small molecule/target pair, or a metal ion/chelating agent pair.

The analyte may be a chemical or biological analyte. The term "analyte," may refer to any chemical, biochemical, or biological entity (e.g. a molecule) to be analyzed. In some cases, the polymeric structure may be selected to have high specificity for the analyte, and may be a chemical, biological, or explosives sensor, for example. In some embodiments, the analyte comprises a functional group that is capable of interacting with at least a portion of the emissive polymer material. For example, the functional group may interact with the outer layer of the article by forming a bond, such as a covalent bond. In some cases, the binding site may determine changes in pH, moisture, temperature, or the like. In one embodiment, the analyte is a biological molecule, such as a protein.

In some embodiments, the outer layer may be appropriately functionalized to impart desired characteristics (e.g., surface properties) to the particle. For example, the outer layer may be functionalized or derivatized to include compounds, functional groups, atoms, or materials that can alter or improve properties of the particle. In some embodiments, the outer layer may include compounds, atoms, or materials that can alter or improve properties such as compatibility with a suspension medium (e.g., water solubility, water stability), photo-stability, and biocompatibility. In some cases, the outer layer comprises a luminescent polymer which may comprise functional groups selected to possess an affinity for a surface. For example, the luminescent polymer may also be functionalized to facilitate adsorption onto a particular surface, such as the surface of a particle, as described herein. In some embodiments, the luminescent polymer is functionalized with carboxylic acid moieties, which may allow for electrostatic adsorption onto charged surfaces, such as glass surfaces, particle surfaces, and the like.

Other properties of the luminescent polymers may be tailored based on substitution of the conjugated polymer backbone, such as a particular band gap or a specific emission wavelength. For example, the polymer may be substituted with electron-poor groups, such as acyl, carboxyl, cyano, nitro, sulfonate, or the like, or the polymer may install electron-poor aryl groups in the backbone of the polymer, such that the polymer exhibits fluorescence emission at shorter wavelengths. In other embodiments, the monomers may be substituted with electron-rich groups, such as amino, hydroxy, alkoxy, acylamino, acyloxy, alkyl, halide, and the like, or the monomers may install electron-rich aryl groups in the backbone of the polymer, such that the polymer exhibits fluorescence emission at longer wavelengths. In some embodiments, the polymer may tailored to advantageously have a large Stokes shift, wherein the fluorescence spectrum is observed at a substantially longer wavelength than the excitation spectrum. In some embodiments, an electron-rich monomer may be co-polymerized with an electron-poor monomer to produce polymers having longer wavelength emission.

In some embodiments, the polymer comprises a sterically bulky monomer that may aid in preserving the optical properties of the polymer or oligomer, even in the solid state. That is, the use of sterically bulky monomers may prevent adjacent or nearby neighboring molecules from interacting with each other through, for example, pi-stacking, to cause a decrease in emission. In some cases, the bulky monomer may comprise a non-planar, bicyclic group that is rigidly attached to the polymer backbone, wherein the bicyclic group comprises bridgehead atoms that are not adjacent to one another. A "rigid" group refers to a group that does not easily rotate about a bond axis, preferably a bond that binds the rigid group to the polymer. In one embodiment, the rigid group rotates no more than about 180°, or, in another embodiment, by no more than about 120°, or by no more than about 60°. Certain types of rigid groups can provide a polymer with a backbone separated from an adjacent backbone at a distance of at least about 4.5 Å, or in another embodiment at least about 5.0 Å. In one embodiment, the rigid groups are incorporated as pendant groups. Examples of bulky monomers may include monomers comprising surfactants, proteins, or sterically large and/or non-planar organic groups such as pentiptycenes having five arene planes, triptycenes having three arene planes, or other iptycene and iptycene-related moieties. By minimizing the intermolecular pi-pi interactions between nearby or adjacent polymers, the shape of the emission spectra may remain substantially the same as the conjugated polymers are formed into particles or are aggregated in the solid-state. In some embodiment, incorporation of pentiptycene units into the main chain of the polymer yields non-aggregating films with superior emissive properties.

Luminescent polymers of the invention may comprises a molecular structure that reduces pi-stacking interactions, resulting in increased quantum yields and/or luminescence lifetimes. These enhanced properties can be achieved when the polymer is provided as a solid state material, e.g. a film. In one embodiment, the film comprising a luminescent polymer has a quantum yield of at least about 0.05 times the quantum yield of the luminescent polymer in solution, or in another embodiment at least about 0.1 times the quantum yield of the luminescent polymer in solution, or at least about 0.15 times the quantum yield of the luminescent polymer in solution, or at least about 0.2 times the quantum yield of the luminescent polymer in solution, or at least about 0.25 times the quantum yield of the luminescent polymer in solution, or at least about 0.3 times the quantum yield of the luminescent polymer in solution, or at least about 0.4 times the quantum yield of the luminescent polymer in solution, or about 0.5 times the quantum yield of the luminescent polymer in solution.

The polymer can be a homo-polymer or a co-polymer such as a random co-polymer or a block co-polymer. In one embodiment, the polymer is a block co-polymer.

Particles of the invention may be coated with a film of luminescent polymer using techniques known in the art, such as electrostatic layer-by-layer desposition, spin-cast methods, and the like. For example, films of luminescent polymer may be formed on the surface of the particles by adding a solution of the luminescent polymer to a suspension of the particles and allowing the polymer to adsorb onto the particles. In some cases, the particles may first be treated (e.g., coated) with a material that may facilitate adsorption of the luminescent polymer. In some cases, the particles may be treated with, for example, poly(ethyleneimine), poly-(styrenesulfonate), or combinations thereof.

Particles of the invention may further comprise an emissive species that may be used as an internal reference standard. The species may be any emissive species, wherein the emission is separated from the emission of the outer layer (e.g., luminescent polymer) by at least 50 nm. In one embodiment, the species may produce an emission upon exposure to the same excitation wavelength as the luminescent polymer, however, the species does not interact with the luminescent polymer, analyte, and/or other components involved in the determination of the analyte. That is, the species may produce an emission signal that does not change in the presence of an analyte. For example, the luminescent polymer may have a first emission and the species may have a second emission which is red-shifted relative to the first emission, wherein the first emission and the second emission may be excited at the same wavelength. The species may be a metal, dye, or other emissive species. For example, the species may be a metal such as a metal particle, quantum dot, or the like, an organic dye, such a fluorescein, Texas Red, and the like, or other emissive species. In one embodiment, the species is europium.

The support material may be any material capable of supporting (e.g., containing) the components (e.g., the metal complex) of the systems described herein. For example, the support material may be selected to have a particular surface area wherein the support material may absorb or otherwise contact a sufficient amount of analyte to allow interaction between the analyte and, for example, the metal complex. In some embodiments, the support material has a high surface area. In some cases, the support material has a surface area of at least 50 $mm^2$, at least 100 $mm^2$, at least 200 $mm^2$, at least 300 $mm^2$, at least 400 $mm^2$, or at least 500 $mm^2$.

In some embodiments, the support material may preferably have a low background signal, substantially no background signal, or a background signal which does not substantially interfere with the signal generated by the metal complex, either in the presence or in the absence of analyte. In some cases, the support material may have a preferred pH to prevent undesirable reactions with, for example, an acid. The support material may be soluble, swellable, or otherwise have sufficient permeability in systems of the invention to permit, for example, intercalation of compounds as described herein, and other components of the system within the support material. Additionally, the support material may preferably permit efficient contact between the sample (e.g., analyte) to be determined and the particles. For example, in one embodiment, a vapor or solution comprising an analyte may permeate the support material to interact with the particle via energy transfer, electron transfer, or the like. The permeability of certain support materials described herein are known in the art, allowing for the selection of a particular support material having a desired diffusion. The choice of support material may also affect the intensity and duration of light emission from the system.

Examples of support materials include polymers, copolymers, gels or hydrogels, and other solid adsorbent materials. In some embodiments, the system may have a shape or be formed into a shape (for example, by casting, molding, extruding, and the like). In some embodiments, the support material may be a polymer. Examples include poly(methyl methacrylate), polyethylene, polypropylene, poly(vinyl chloride), poly(vinyl benzoate), poly(vinyl acetate), cellulose, corn starch, poly(vinyl pyrrolidinone)s, polyacrylamides, epoxys, silicones, poly(vinyl butyral)s, polyurethanes, nylons, polacetals, polycarbonates, polyesters and polyethers, polybutadiene copolymers, crosslinked polymers, combinations thereof, and the like.

In some cases, the support material is a hydrogel. Polymer gels or hydrogels may be characterized by long chain polymer molecules that are crosslinked to form a network, wherein the network may be able to trap and hold fluid, which can give gels properties somewhere between those of solids and liquids. In the design of gels for a particular application, the degree of crosslinking may be adjusted to achieve the desired compromise between speed of absorption and level of structural integrity. Those of ordinary skill in the art would be able to identify methods for modulating the degree of crosslinking in such gels. Some examples of hydrogels include polyacrylamides, silicon hydrogels, polyethylene oxides, polyvinylpyrrolidones, polyvinyl alcohols, polyacrylates, other polymers comprising hydrophilic groups, combinations thereof, and the like. In one embodiment, the support material comprises polyacryamide and poly(N,N'-dimethylenebisacrylamide).

The permeability of a particular polymer is known in the art. The support material may be selected to have a particular desired diffusion rate, controlling the intensity and duration of light emission.

EXAMPLES

Example 1

Monomers A, C, and D were synthesized according to literature procedures. Diethynylpentiptycene (B) was purchased from Nomadics Life Sciences Inc. Pd(PPh$_3$)$_4$ and CuI were purchased from Strem. All solvents for polymerization were obtained from Aldrich and degassed by rapid sparging with argon for 20 minutes before use. Bio Beads S-3 (Bio-Rad Laboratories) used for size exclusion chromatography were pre-swelled in DMF overnight before use. N,N-dimethylformamide (DMF, HPLC grade), Tris(hydroxymethyl)aminomethane buffer, sodium chloride, calcium chloride, and methyl viologen dichloride (MV$^{2+}$) were purchased from Aldrich and used as received. 1-methyl-1'-naphthalen-2-yl methyl-[4,4'] bipyridinyl dication dichloride (MV$^{2+}$-nap) was previously synthesized in a separate report. Polymer molecular weights were determined using gel permeation chromatography in THF solution vs. PS standards. $^1$H NMR spectra were recorded on a 500-MHz Varian Unity instrument. All photophysical measurements were performed at room temperature using a 1 cm-path length quartz cuvette in right-angle detection mode. Absorbance was measured using a Cary 50 or Agilent 845 UV-Vis spectrophotometer, corrected for solvent or substrate baseline. Steady-state fluorescence and lifetime spectra were acquired using a Jobin Yvon SPEX Fluorolog-τ2 or -τ3 fluorimeter. Solution lifetimes were measured using the frequency domain method, with 10 frequencies ranging from 10-250 MHz, fit to a single exponential. Quantum yields in solution were obtained by the reference method using coumarin 6 in ethanol as standard ($\Phi_F$=0.78).

Carboxylate-modified europium microspheres (d=0.2 μm) were purchased from Invitrogen and used after rinsing with deionized water. Amine-modified polystyrene microspheres (d=0.52 μm) for zeta potential measurements were purchased from Bangs Laboratories and used after rinsing with deionized water. Poly(ethyleneimine) (PEI, branched, MW 10 kDa) and poly(styrene sulfonic acid) sodium salt (PSS, MW 500 kDa) were obtained from Polysciences. Deionized water purified through a 0.2 μm syringe filter was used for all aqueous measurements and preparation of solutions. All solutions for electrostatic adsorption were prepared in 1×10$^{-3}$ M per repeat unit in water for PEI and PSS, or a 10:90 mixture of DMF:water for P1-P3 due to limited solubility in water. Glass slides for monitoring film adsorption were used as received from VWR and coated with a pre-layer of PEI/PSS/PEI before adsorbing P1-P3.

Example 2

The polymers were synthesized according to the following general procedure, using Pd-catalyzed Sonagashira coupling reactions between respective diacetylene and diiodide monomers in quantitative yield.

Monomers were added to an 10 mL Schlenk tube with a stir bar and evacuated and purged with nitrogen before addition of Pd(PPh$_3$)$_4$ and CuI (catalytic amounts) in a glovebox. 1.5 mL of 5:4:1 (v/v) N-methylpyrrolidone:toluene:diisopropylae, degassed with rapid sparging of argon, was added to the flask, for complete solubility of the starting materials. The flask was sealed and heated for 72 hours at 65° C., after which the solution turned from a milky white color to yellow with bright green fluorescence. After removing from heat, ethyl acetate was added to precipitate the reaction mixture to a yellow solid, which was subsequently purified using size exclusion chromatography with DMF as the eluent to yield the product polymers.

Polymer P1 was synthesized according to the above procedure using monomer A (35 mg, 0.051 mmol) and monomer B (25 mg, 0.053 mmol), as shown in FIG. 3A (72%). $^1$H NMR (500 MHz, DMF-d$_7$): broad peaks centered around (in ppm) 2.3-2.5, 3.7, 4.1-4.6, 5.0, 6.4, −6.7, 7.1, 7.4, 7.7.

Polymer P2 was synthesized according to the above procedure using monomer A (15 mg, 0.022 mmol), monomer B (21 mg, 0.045 mmol), and monomer C 17 mg, 0.022 mmol), as shown in FIG. 3B (69%). $^1$H NMR (500 MHz, DMF-d$_7$): broad peaks centered around (in ppm) 3.5-3.7, 4.1-4.8, 6.4-6.7, 7.1, 7.4, 7.7.

Polymer P3 was synthesized according to the above procedure using monomer A (11 mg, 0.016 mmol), monomer B (16 mg, 0.033 mmol), and monomer D (9 mg, 0.016 mmol), as shown in FIG. 3C (76%). $^1$H NMR (500 MHz, DMF-d$_7$): broad peaks centered around (in ppm) 2.1-2.5, 3.6, 4.2-4.8, 5.4, 6.3-6.7, 7.1, 7.4, 7.7.

The carboxylate groups were not sufficiently soluble to allow for molecular weight determinations and, thus, were converted to dibutylamide groups to provide solubility characteristics that allow analysis by gel permeation chromatography. Polymers P1-P3 were activated with excess molar ratio of EDAC/NHS in DMF, and then subsequent addition of excess dibutylamine for a reaction time of 12 hours, to afford a product that could be eluted from THF (Polymers P1e, P2e, and P3e). GPC analysis of the modified polymers was performed to determine the molecular weight of the amide-modified polymers. Polymers P1e, P2e, and P3e in DMF showed number-average molecular weights of 370 kDa (PDI=1.8), 590 kDa (PDI=1.2), and 22 kDa (PDI=1.1), respectively. GPC analysis. P1e: GPC: M$_n$=7 kDa, PDI=1.4. P2e: GPC: M$_n$=8 kDa, PDI=1.5. P3e: GPC: M$_n$=17 kDa, PDI=2.2.

Example 3

In order to optically monitor the layering process of PPEs (e.g., P1-P3) on a substrate, a series of polymer films were sequentially formed on glass slides prelayered with PEI:PSS:PEI, and the absorbance of each PPE film layer was measured. The first PPE film layer was formed by dipping a glass slide prelayered with PEI:PSS:PEI in a solution of PPE (1×10$^{-3}$ M) for 15 minutes, following by rinsing with deionized water and drying with nitrogen stream. The absorbance of the film was then measured. To form the second PPE film layer, the slide was first dipped in PEI for 15 minutes, rinsed with water, and then dipped in the PPE solution as described above, for subsequent layers. For each glass slide, a total of four PPE layers was deposited, with a PEI layer in between each PPE layer.

Figure 4:
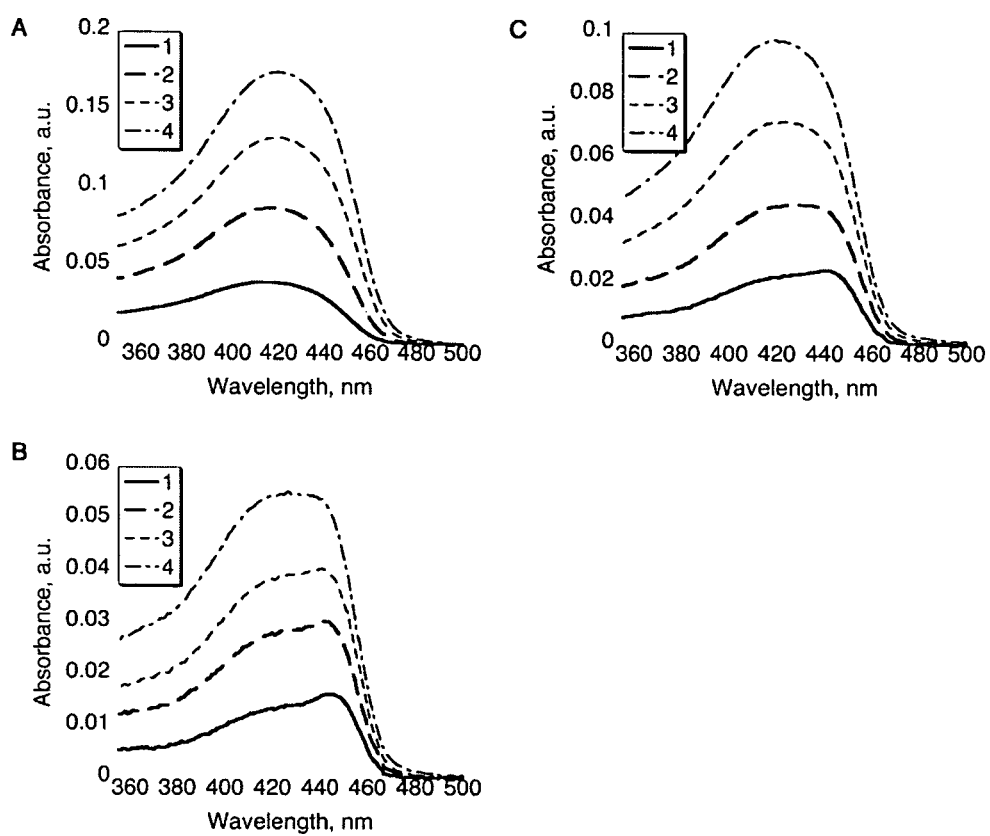
FIG. 4A shows the absorption spectra for a film of P1-coated particles, for 1, 2, 3, and 4 layers of P1.
FIG. 4B shows the absorption spectra for a film of P2-coated particles, for 1, 2, 3, and 4 layers of P2.
FIG. 4C shows the absorption spectra for a film of P3-coated particles, for 1, 2, 3, and 4 layers of P3.

FIG. 4A shows the absorption spectra for a film of P1-coated particles, for 1, 2, 3, and 4 layers of P1. FIG. 4B shows the absorption spectra for a film of P2-coated particles, for 1, 2, 3, and 4 layers of P2. FIG. 4C shows the absorption spectra for a film of P3-coated particles, for 1, 2, 3, and 4 layers of P3.

Figure 5:
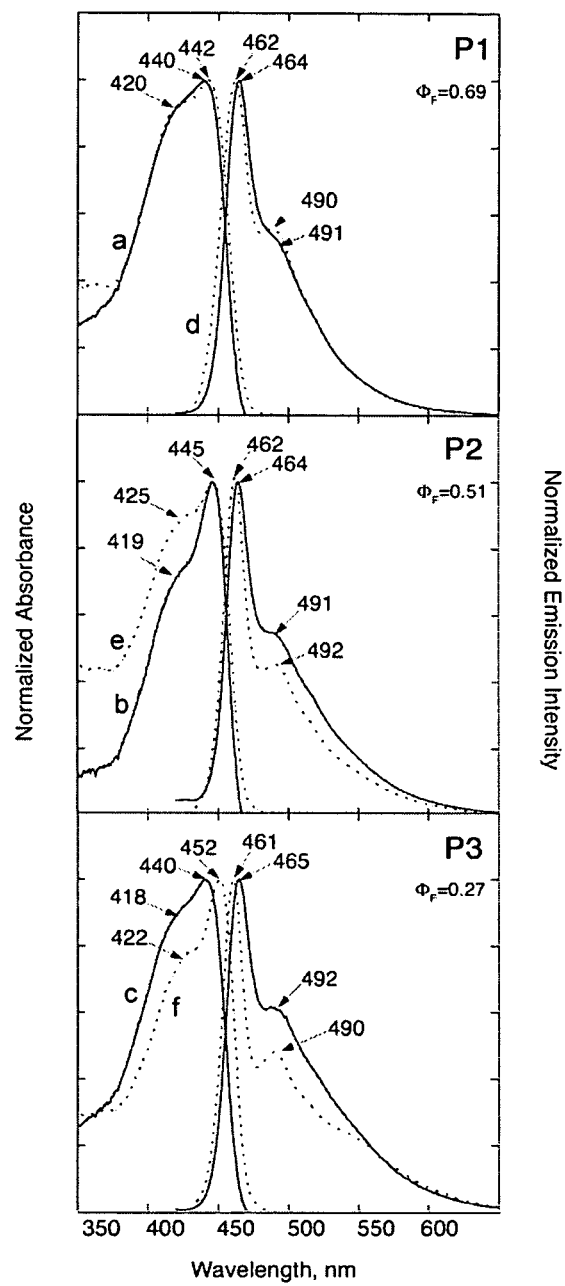
FIG. 5 shows the absorption and fluorescence spectra for (a) P1-coated films, (b) P2-coated films, (c) P3-coated films, (d) P1 in DMF solution, (e) P2 in DMF solution, (f) P3 in DMF solution.

The absorption and fluorescence spectra for the PPE-coated films are shown in FIG. 5 for (a) P1-coated films, (b) P2-coated films, and (c) P3-coated films, (d) P1 in DMF solution, (e) P2 in DMF solution, (f) P3 in DMF solution. Quantum yields ($\Phi_F$) are in DMF solution referenced to coumarin 6 in EtOH as standard ($\Phi_F$=0.78). The solution and thin film spectra were observed to be nearly identical, demonstrating the capability of the bulky pentiptycene substituents to eliminate interchain aggregation in the solid-state.

Example 4

The process to produce thin films on the particles was similar to that used for the flat substrate; however, since the Eu—PS particles were carboxylate-functionalized, a pre-layer of PEI was adsorbed on the particles before immobilization of P1-P3. In some cases, the microspheres were initially coated with a trilayer film of poly(ethyleneimine):poly-(styrenesulfonate):poly(ethyleneimine) (PEI:PSS:PEI) to minimize defects.

To prepare P1-coated particles, the method of electrostatic layer-by-layer deposition was used. Carboxylate-functionalized europium-polystyrene particles (adjusted to a concentration of 0.025% solids) were dispersed in poly(ethylenimine) solution for 15 minutes, followed by a washing procedure (involving centrifugation, removal of the supernatant, and rinsing with water) repeated twice to remove any excess polymer. The P1 solution was then added for an adsorption time of 15 minutes, removed and washed twice with water. The polymer-coated particles were then resuspended in deionized water, Tris buffer (20 mM, pH 7.4), and Tris-buffered saline (20 mM, pH 7.4; 150 mM NaCl; 5 mM CaCl$_2$) for subsequent quenching experiments.

P2-coated particles and P3-coated particles were also prepared in the same manner for experiments.

Example 5

To prepare PPE-coated particles, an electrostatic layer-by-layer deposition method was used. Carboxylate-functionalized europium-polystyrene (Eu—PS) particles, adjusted to a concentration of 0.025% solids, were dispersed in poly(ethylenimine) solution for 15 minutes, followed by a washing procedure that involved centrifugation, removal of the supernatant, and rinsing with water. The washing procedure was repeated twice. To form a P1-coated particle, a P1 solution was then added for an adsorption time of 15 minutes, removed and washed twice with water before final resuspension in medium. P2-coated particles and P3-coated particles were also prepared in the same manner for experiments.

Figure 6:
FIG. 6 shows a confocal image of P1-coated Eu—PS particles in deionized water.

Confocal microscopy images of the coated particles were taken on a Leica TCS-SP2 confocal laser scanning microscope using an argon 360 nm laser as the excitation source and a 63×/1.4 oil immersion lens. The images showed the emission of the particles from the PPE coating. For example, FIG. 6 shows a confocal image of P1-coated Eu—PS particles in deionized water.

Example 6

The zeta potential of polymers adsorbed onto amine-functionalized polystyrene particles, with an adsorption time of 15 minutes, was measured using a ZetaPals Zeta Potential Analyzer (Brookhaven Instruments Corporation) in a 1-cm polystyrene cuvette with Millipore water, Tris 20 mM pH=7.4, or Tris-buffered saline (Tris 20 mM, 150 mM NaCl, 20 mM CaCl$_2$ as solvent. Mean zeta potential is reported based on 10 runs of 25 cycles, and converting mobility to zeta potential using the Smoluchowski equation ($\zeta = \mu \eta / \epsilon$, where $\zeta$ is the zeta potential, $\mu$ is the electrophoretic mobility, $\eta$ is the viscosity, and $\epsilon$ is the electric permittivity of the liquid). The zeta potential for particles coated with P1, P2, and P3 is shown in Table 1.

TABLE 1

Apparent zeta potential (in mV) of polymer-coated particles.

| Polymer | Water | Tris 20 mM, pH = 7.4 | Tris-buffered saline |
|---------|-------|----------------------|----------------------|
| P1 | −54.6 ± 0.6 | −29.1 ± 0.7 | −15.2 ± 1.1 |
| P2 | −26.3 ± 0.6 | −13.8 ± 1.2 | −4.75 ± 1.9 |
| P3 | −31.3 ± 0.7 | −26.8 ± 1.1 | −11.1 ± 1.1 |

Example 7

Figure 7:
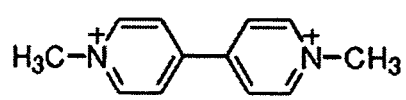
FIG. 7 shows methyl viologen ($MV^{2+}$) and a napthyl-derivative of methyl viologen ($MV^{2+}$-nap), which may be used as analytes in some embodiments of the invention.
Figure 7:
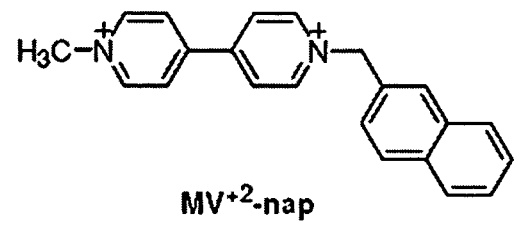

A series of poly(phenylene ethynylene)s (PPE)s, P1-P3, was studied as films supported on europium-incorporated polystyrene particles (d=0.2 µm) for their fluorescence quenching response towards viologens, which are well-known electron-accepting aromatic molecules. The viologens used in this experiment were methyl viologen (MV$^{2+}$) and a napthyl-derivative of methyl viologen (MV$^{2+}$-nap), as shown in FIG. 7. The luminescence responses of the polymers to both MV$^{2+}$ and MV$^{2+}$-nap were evaluated to determine the influence of the hydrophobic character of an analyte in promoting interactions with the polymer films.

Stock solutions of 1.0 and 0.1 mM were prepared for each viologen and experimental condition. For solution quenching, quencher stock solutions were made from polymer stock solution (1×10$^{-6}$ M per repeat unit) to avoid dilution effects. For each experiment, the initial fluorescence emission intensity was measured. Aliquots of the quencher stock solution were added to a suspension of the coated particles in a cuvette and the fluorescence was measured after 5 minutes to allow for equilibration. Excitation wavelengths used for solution and particle quenching were 405 nm and 390 nm, respectively, the latter allowing for the excitation of the euriopium internal reference. Measurements were performed in triplicate with R-squared values of >0.98 for each condition.

Excitation of the coated particles at 390 nm allowed for direct excitation of both the polymer and the Eu incorporated in the PS particles. FIG. 8 shows the response of P1-coated particles in Tris buffer (20 mM, pH 7.4) towards MV$^{2+}$-nap, with Eu as reference at 612 nm, in response to the addition of (a) 0.00 µM, (b) 0.06 µM, (c) 0.12 µM, and (d) 0.18 µM of MV$^{2+}$-nap. FIG. 8 also shows (e) the Eu reference peak and (f) the Stern-Volmer plot of R$_0$/R vs. [MV$^{2+}$-nap] with linear best fit. Normalization of the spectra to the Eu peak at 612 nm can account for fluctuations in the particle dispersion and for an accurate measure of the quenching response.

Figure 9:
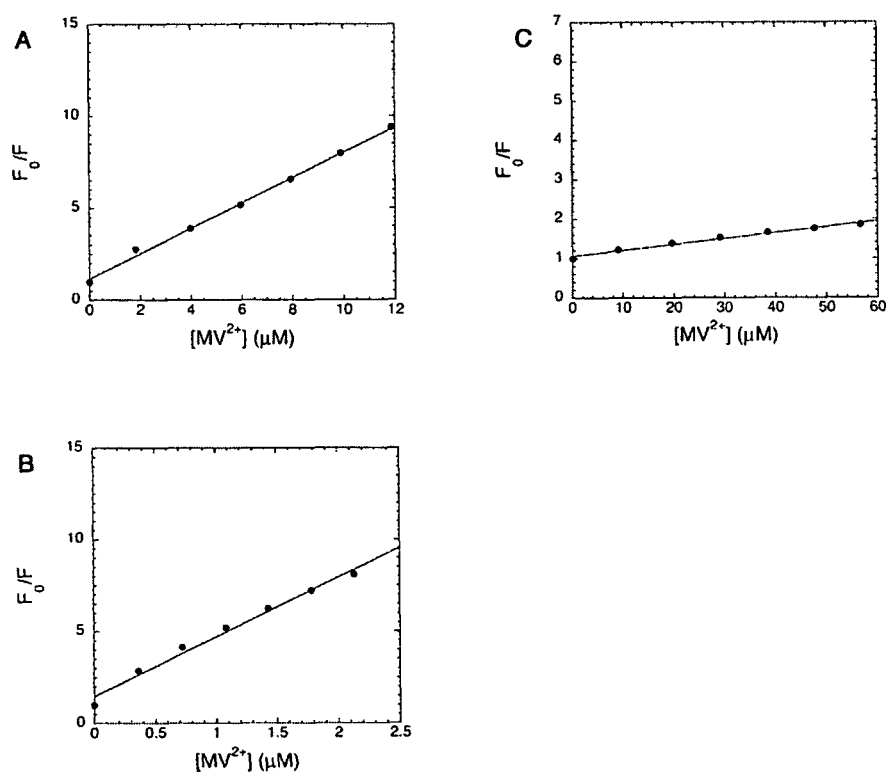
FIG. 9 shows Stem-Volmer plots of (a) P1-coated particles, (b) P2-coated particles, and (c) P3-coated particles in response to exposure to $MV^{2+}$ in DMF solution.

FIG. 9 shows Stern-Volmer plots of (a) P1-coated particles, (b) P2-coated particles, and (c) P3-coated particles in response to exposure to $MV^{2+}$ in DMF solution.

Figure 10:
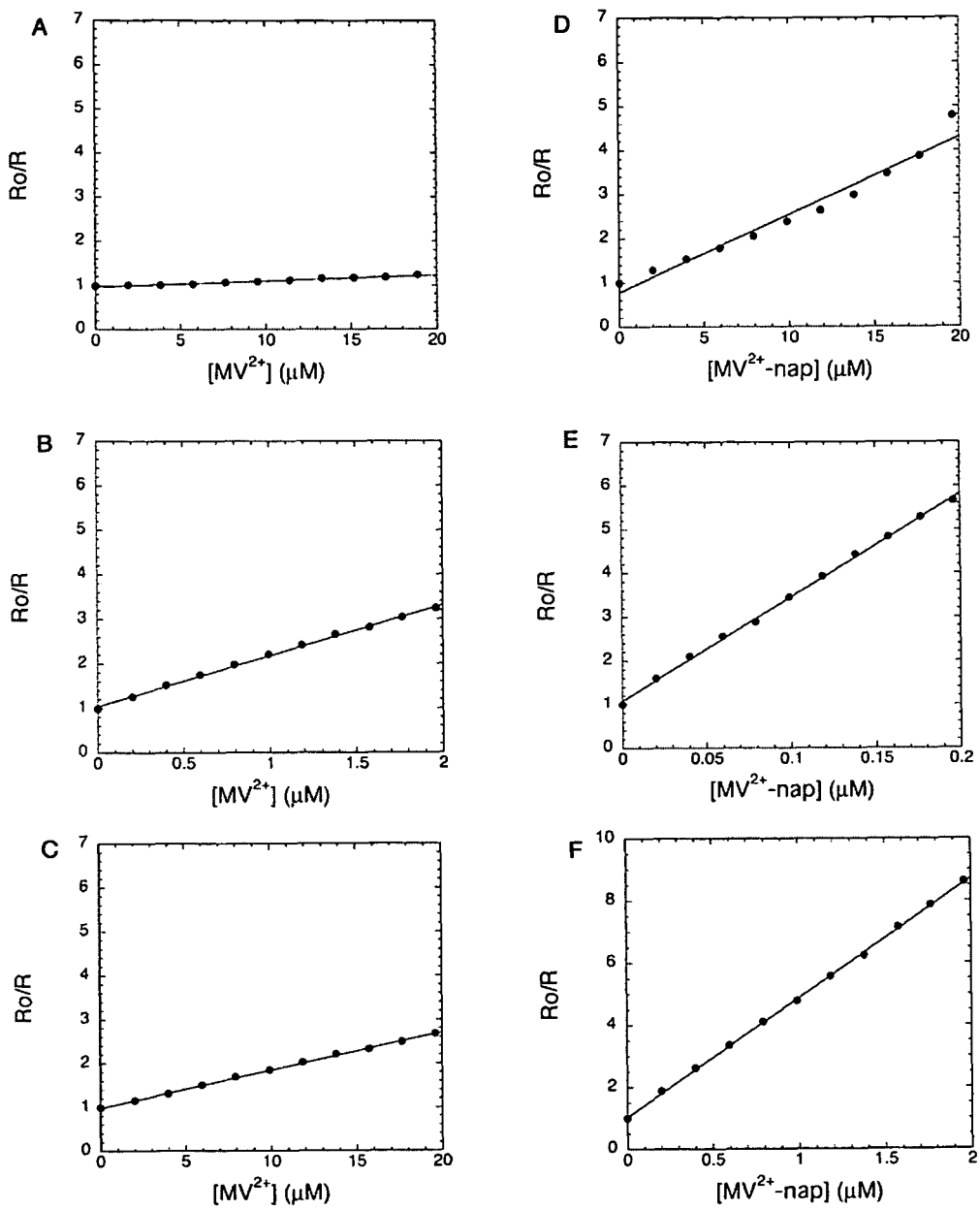
FIG. 10 shows Stem-Volmer plots of P1-coated particles in response to (a) $MV^{2+}$ in water, (b) $MV^{2+}$ in Tris buffer (20 mM, pH 7.4), (c) $MV^{2+}$ in Tris-buffered saline (20 mM, pH 7.4; 150 mM NaCl, 5 mM $CaCl_2$), (d) $MV^{2+}$-nap in water, (e) $MV^{2+}$-nap Tris buffer (20 mM, pH 7.4), and (f) $MV^{2+}$-nap in Tris-buffered saline (20 mM, pH 7.4; 150 mM NaCl, 5 mM $CaCl_2$).

FIG. 10 shows Stern-Volmer plots of P1-coated particles in response to (a) $MV^{2+}$ in water, (b) $MV^{2+}$ in Tris buffer (20 mM, pH 7.4), (c) $MV^{2+}$ in Tris-buffered saline (20 mM, pH 7.4; 150 mM NaCl, 5 mM $CaCl_2$), (d) $MV^{2+}$-nap in water, (e) $MV^{2+}$-nap Tris buffer (20 mM, pH 7.4), and (f) $MV^{2+}$-nap in Tris-buffered saline (20 mM, pH 7.4; 150 mM NaCl, 5 mM $CaCl_2$).

Figure 11:
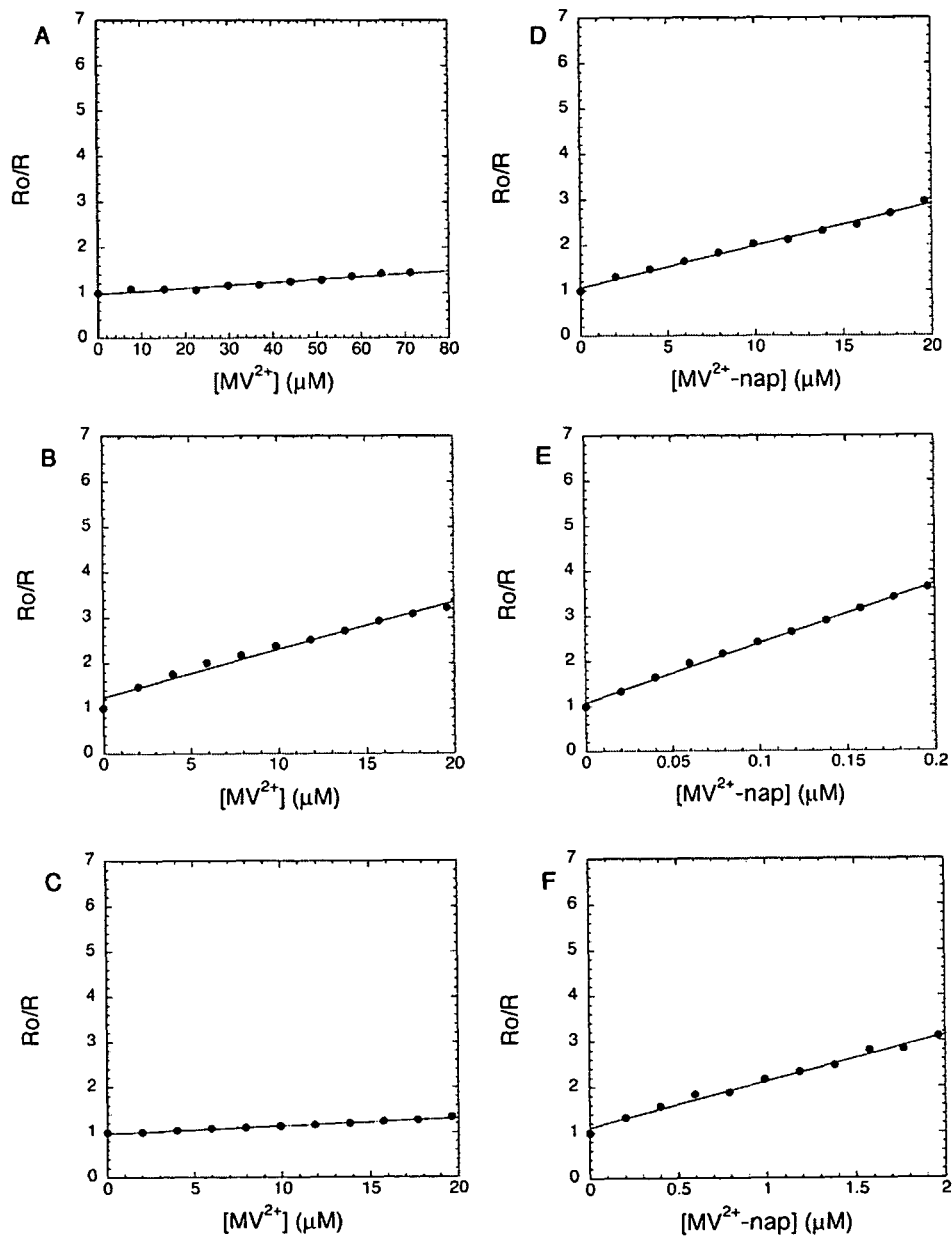
FIG. 11 shows Stern-Volmer plots of P2-coated particles in response to (a) $MV^{2+}$ in water, (b) $MV^{2+}$ in Tris buffer (20 mM, pH 7.4), (c) $MV^{2+}$ in Tris-buffered saline (20 mM, pH 7.4; 150 mM NaCl, 5 mM $CaCl_2$), (d) $MV^{2+}$-nap in water, (e) $MV^{2+}$-nap Tris buffer (20 mM, pH 7.4), and (f) $MV^{2+}$-nap in Tris-buffered saline (20 mM, pH 7.4; 150 mM NaCl, 5 mM $CaCl_2$).

FIG. 11 shows Stern-Volmer plots of P2-coated particles in response to (a) $MV^{2+}$ in water, (b) $MV^{2+}$ in Tris buffer (20 mM, pH 7.4), (c) $MV^{2+}$ in Tris-buffered saline (20 mM, pH 7.4; 150 mM NaCl, 5 mM $CaCl_2$), (d) $MV^{2+}$-nap in water, (e) $MV^{2+}$-nap Tris buffer (20 mM, pH 7.4), and (f) $MV^{2+}$-nap in Tris-buffered saline (20 mM, pH 7.4; 150 mM NaCl, 5 mM $CaCl_2$).

Figure 12:
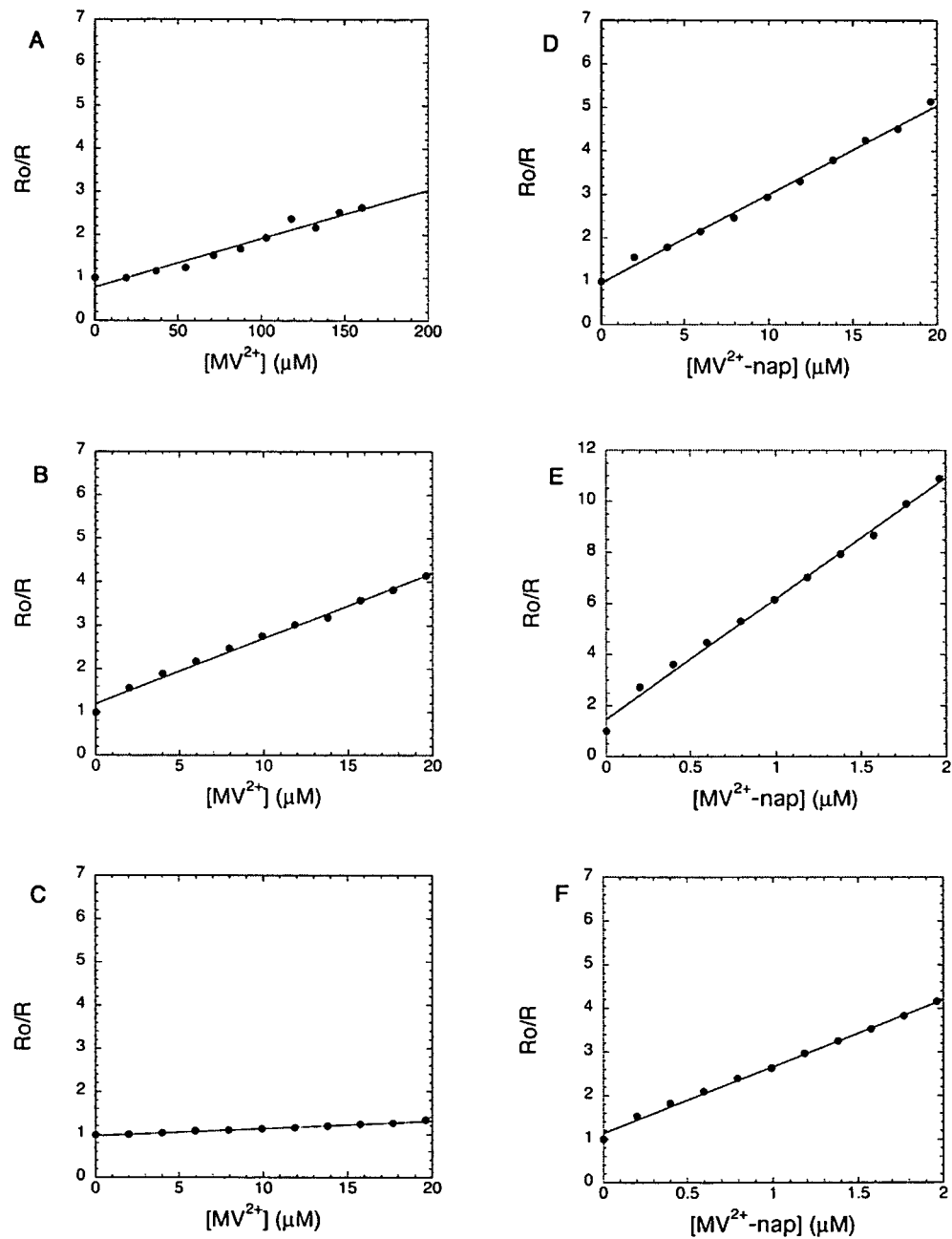
FIG. 12 shows Stern-Volmer plots of P2-coated particles in response to (a) $MV^{2+}$ in water, (b) $MV^{2+}$ in Tris buffer (20 mM, pH 7.4), (c) $MV^{2+}$ in Tris-buffered saline (20 mM, pH 7.4; 150 mM NaCl, 5 mM $CaCl_2$), (d) $MV^{2+}$-nap in water, (e) $MV^{2+}$-nap Tris buffer (20 mM, pH 7.4), and (f) $MV^{2+}$-nap in Tris-buffered saline (20 mM, pH 7.4; 150 mM NaCl, 5 mM $CaCl_2$).

FIG. 12 shows Stern-Volmer plots of P2-coated particles in response to (a) $MV^{2+}$ in water, (b) $MV^{2+}$ in Tris buffer (20 mM, pH 7.4), (c) $MV^{2+}$ in Tris-buffered saline (20 mM, pH 7.4; 150 mM NaCl, 5 mM $CaCl_2$), (d) $MV^{2+}$-nap in water, (e) $MV^{2+}$-nap Tris buffer (20 mM, pH 7.4), and (f) $MV^{2+}$-nap in Tris-buffered saline (20 mM, pH 7.4; 150 mM NaCl, 5 mM $CaCl_2$).

Figure 13:
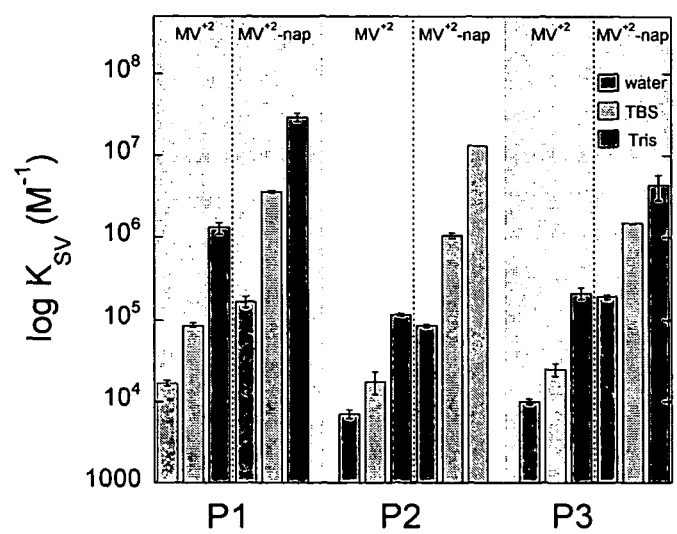
FIG. 13 shows a summary of Ksv values for P1-P3 in response to $MV^{+2}$ and $MV^{+2}$-nap in deionized water, Tris buffer (Tris, 20 mM, pH 7.4), and Tris-buffered saline (TBS, 20 mM, pH 7.4; 150 mM NaCl, 5 mM $CaCl_2$).

FIG. 13 shows a summary of $K_{SV}$ values for P1-P3 in response to $MV^{+2}$ and $MV^{+2}$-nap in deionized water, Tris buffer (Tris, 20 mM, pH 7.4), and Tris-buffered saline (TBS, 20 mM, pH 0.7.4; 150 mM NaCl, 5 mM $CaCl_2$). Error bars indicate standard errors based on triplicate measurements for each experimental condition. The magnitude of quenching observed exceeded the diffusion limit and indicated that static quenching may be operative. A linear best fit yielded a Stern-Volmer quenching constant of $(2.9\pm0.3)\times10^7$ $M^{-1}$.

Table 2 shows the quenching constant data for the coated particles in response to $MV^{2+}$, and Table 3 shows the quenching constant data for the coated particles in response to $MV^{2+}$-nap.

Overall, P1-coated particles were observed to exhibit a larger quenching response towards the quenchers, which may be attributed to the greater charge density of P1-coated particles relative to P2-coated particles and P3-coated particles. The difference in behavior among the polymers was notable upon exposure to $MV^{+2}$. The response towards $MV^{+2}$-nap of P2 and P3, however, were not considerably lower than that of P1, particularly in water, where electrostatic interactions were strongest, suggesting that there may be a dominance of the hydrophobic interactions between the napthyl rings with the pentiptycene backbone in an aqueous environment relative to the electrostatic interactions of the quaternary amines with the polymer-dependent number of carboxylate side chains.

The responses of P2-coated particles and P3-coated particles were similar for the same conditions. This is in contrast to their behavior in DMF solution, where P2-coated particles ($K_{SV}=(2.9\pm0.2)\times10^6$ $M^{-1}$) showed a greater quenching response towards $MV^{+2}$ relative to P3-coated particles ($K_{SV}=(1.9\pm0.4)\times10^4$ $M^{-1}$). The quenching response of P2-coated particles in DMF solution was even greater than the quenching response displayed by P1 ($K_{SV}=(4.3\pm1)\times10^5$ $M^{-1}$), illustrating that the macrocycles efficiently bind $MV^{+2}$ through hydrogen bonding and $\pi$-$\pi$ interactions, thereby giving an increase in the overall sensitivity.

In the microsphere system, no significant differences between the behavior of P2-coated particles and P3-coated particles towards the viologen quenchers were observed. The disparity between solution and film behavior may be due to the film formation process, wherein the receptors are geometrically constrained and cannot effectively enhance interactions with the quenchers. Spatially-organized films such as the Langmuir-Blodgett type, in which a single monolayer can be deposited, may prove to be a better arrangement for the activity of flexible molecular receptors in aqueous solution.

Quenchers $MV^{+2}$ and $MV^{+2}$-nap followed similar trends over all of the conditions investigated, with the highest observed quenching in Tris buffer (20 mM, pH 7.4). In this environment, there may be a combination of electrostatic and hydrophobic forces. Increased ionic strength shielded the electrostatic effects and Tris-buffered saline displayed lower $K_{SV}$ values compared to Tris buffer. Interestingly, measurements conducted in Tris-buffered saline also revealed a higher degree of quenching than in pure water. This observation was in contrast to what had been observed for other conjugated polyelectrolytes in solution, wherein buffer conditions shield the electrostatic forces and thus reduce the amount of quenching in electrolyte versus water.

The zeta potential of the polymer-coated particles (Table 1) indicated the effective charge for each experimental condition. Although water generally imparts greater net negative charge, the observed quenching was the lowest in pure water for all polymers, suggesting that the hydrophobic interactions for the PPEs can contribute to a greater extent than the electrostatic interactions. This effect can produce $K_{SV}$ values for $MV^{+2}$-nap that are more than an order of magnitude higher than $MV^{+2}$.

TABLE 2

Quenching constant data for polymer-coated particles P1–P3 in response to $MV^{2+}$.

| | | $K_{SV}(M^{-1})$ | |
| Polymer | Water | Tris 20 mM, pH = 7.4 | Tris-buffered saline |
| --- | --- | --- | --- |
| P1 | $(1.7 \pm 0.6) \times 10^4$ | $(1.3 \pm 0.2) \times 10^6$ | $(8.5 \pm 0.6) \times 10^4$ |
| P2 | $(6.9 \pm 0.7) \times 10^3$ | $(1.1 \pm 0.05) \times 10^5$ | $(1.7 \pm 0.5) \times 10^4$ |
| P3 | $(1.0 \pm 0.7) \times 10^4$ | $(2.1 \pm 0.3) \times 10^5$ | $(2.4 \pm 0.4) \times 10^4$ |

TABLE 3

Quenching constant data for polymer-coated particles P1–P3 in response to $MV^{2+}$-nap.

| | | $K_{SV}(M^{-1})$ | |
| Polymer | Water | Tris 20 mM, pH = 7.4 | Tris-buffered saline |
| --- | --- | --- | --- |
| P1 | $(1.7 \pm 0.3) \times 10^5$ | $(2.9 \pm 0.3) \times 10^7$ | $(3.6 \pm 0.2) \times 10^6$ |
| P2 | $(8.4 \pm 0.4) \times 10^4$ | $(1.3 \pm 0.01) \times 10^7$ | $(1.1 \pm 0.08) \times 10^6$ |
| P3 | $(1.9 \pm 0.1) \times 10^5$ | $(4.3 \pm 1) \times 10^6$ | $(1.5 \pm 0.03) \times 10^6$ |

Example 8

Figure 14:
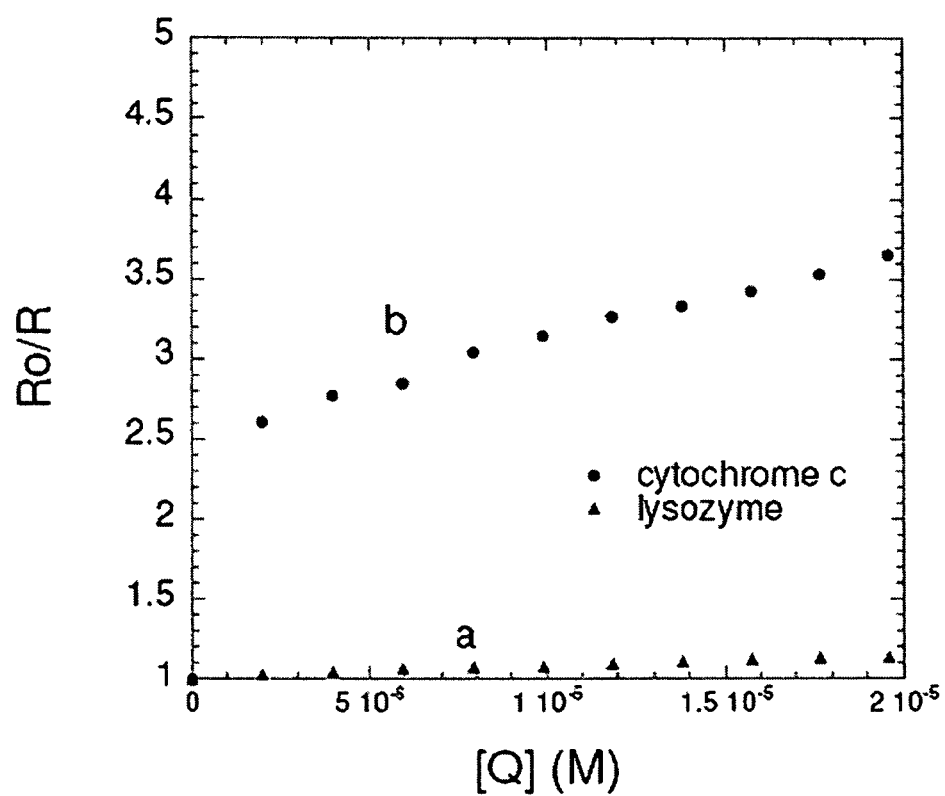
FIG. 14A shows the response of the microspheres towards lysozyme in Tris buffer (20 mM, pH 7.4), plotted as the initial ratio of the PPE and europium peaks divided by the ratio at a specific quencher (Q) concentration.
FIG. 14B shows the response of the microspheres towards cytochrome c in Tris buffer (20 mM, pH 7.4), plotted as the initial ratio of the PPE and europium peaks divided by the ratio at a specific quencher (Q) concentration.

The non-specific quenching ability of PPE/Eu—PS microspheres in the presence of various proteins in solution was investigated. A lysozyme protein was added to a suspension of PPE/Eu—PS microspheres in Tris buffer (20 mM, pH 7.4). FIG. 14A shows the response of the microspheres towards lysozyme in Tris buffer (20 mM, pH 7.4), plotted as the initial ratio of the PPE and europium peaks divided by the ratio at a specific quencher (Q) concentration, wherein a positive slope indicates a decrease in the PPE emission upon addition of quencher. The same experiment was conducted in the presence of cytochrome, and FIG. 14B shows the response of the microspheres towards lysozyme in Tris buffer (20 mM, pH 7.4).

Non-specific quenching was observed between the PPE-coated particles and the proteins in solution, largely due to electrostatic interactions.

Example 9

Figure 15:
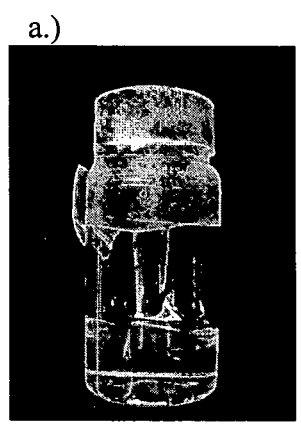
FIG. 15 shows europium-doped polystyrene particles coated with a luminescent polymer, suspended in a hydrogel matrix under (a) ambient light (b) UV light.
Figure 15:
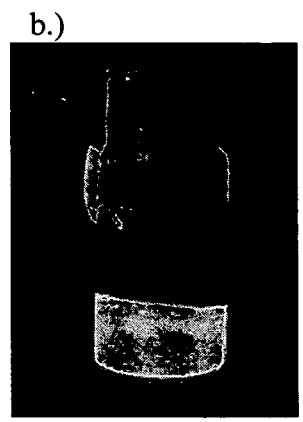

PPE/Eu—PS particles were incorporated into a hydrogel matrix by adding the particles to a solution containing hydrogel precursors (e.g., monomers) and performing solution polymerization or photopolymerization methods known in the art to form the hydrogel. In one case, a mixture of acrylamide, N,N'-dimethylenebisacrylamide, Tris buffer (20 mM, pH 8.2), PPE/Eu—PS particles, ammonium persulfate, and N,N,N',N'-tetramethylethylenediamine (TEMED) was polymerized to give a homogenous luminescent hydrogel. FIG. 15 shows the PPE/Eu—PS particles suspended in the hydrogel under (a) ambient light (b) UV light.

Example 10

Figure 16:
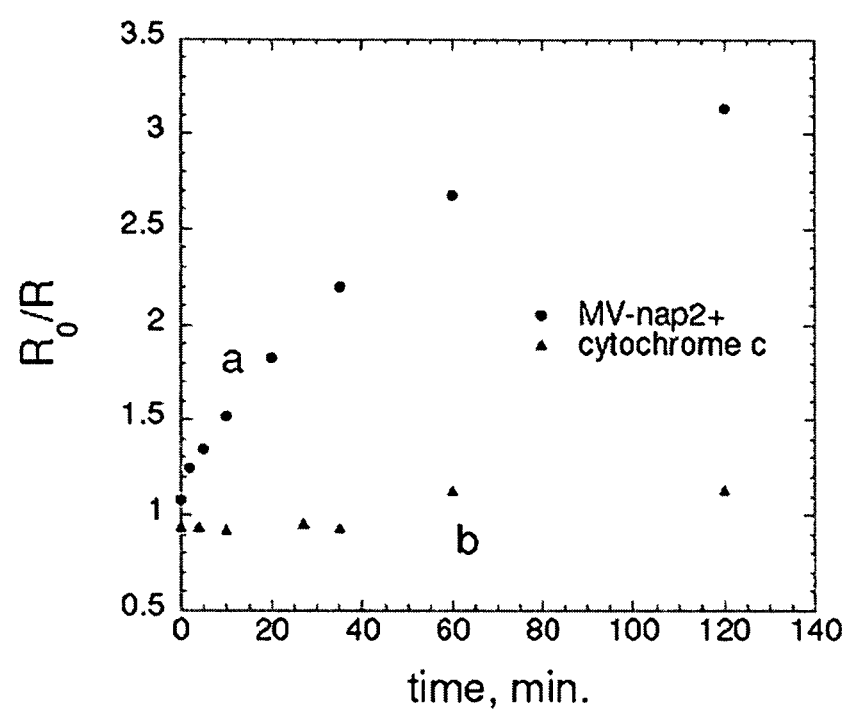
FIG. 16 shows the plot of $R_0/R$ vs. time upon addition of (a) MV-nap$^{2+}$ and (b) cytochrome c to a hydrogel containing europium-doped polystyrene particles coated with a luminescent polymer.

The specific quenching ability of PPE/Eu—PS microspheres dispersed within a hydrogel matrix in the presence of a small molecule quencher ($MV^{2+}$-nap) and a large protein (cyclochrome c) was investigated. MV-nap$^{2+}$ and cytochrome c were added to the hydrogel containing the suspension of PPE/Eu—PS particles, and the fluorescence emission of the PPE was observed. FIG. 16 shows the plot of $R_0/R$ vs. time (min.) upon addition of (a) MV-nap$^{2+}$ and (b) cytochrome c to the hydrogel containing the PPE/Eu—PS particles. The positive slope indicates a decrease in the PPE emission upon addition of quencher. As shown in FIG. 16, addition of the small molecule quencher, MV-nap$^{2+}$, results in a rapid decrease or quenching of PPE emission, whereas non-specific quenching was observed upon addition of a large protein. This suggests that the crosslinked nature of the hydrogel may allow for transport of small molecular species, such as MV-nap$^{2+}$, whereas larger species, such as proteins, cannot easily diffuse through the hydrogel, and thus cannot interact with the contained particles.

This demonstrates the selective diffusion of an analyte through the support material.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A particle, comprising:
a core comprising a polymer that is substantially non-luminescent in the visible region,
an outer layer at least partially encapsulating the core, wherein the outer layer comprises a luminescent polymer having a pi-conjugated backbone and having a first emission upon exposure to a set of conditions, wherein the pi-conjugated backbone has the structure

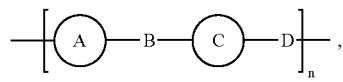

wherein n is at least 1, A and C are aromatic groups, optionally substituted, and B and D are alkene, alkyne, heteroalkene, or heteroalkyne; and
a plurality of luminescent metal species having a second emission upon exposure to said set of conditions, wherein at least a portion of the plurality of metal species is integrally connected to the core.

2. A particle as in claim 1, wherein a characteristic of the first emission is affected by an analyte for determination by the particle, and the second emission is essentially unaffected by the analyte.

3. A particle as in claim 1, wherein the characteristic is luminescence intensity.

4. A particle as in claim 1, wherein the core comprises polystyrene, polyacrylate, poly(methyl methacrylate), polyethylene, polypropylene, poly(vinyl chloride), poly(vinyl benzoate), poly(vinyl acetate), polyacrylamide, poly(vinyl butyral), polyurethane, polyacetal, polycarbonate, polyester, polyether, polybutadiene, substituted derivatives thereof, or combinations thereof.

5. A particle as in claim 1, wherein the core comprises polystyrene.

6. A particle as in claim 1, wherein the species is dispersed throughout the core.

7. A particle as in claim 1, wherein the species is dispersed throughout the outer layer.

8. A particle as in claim 1, wherein the species is europium.

9. A particle as in claim 1, wherein the core comprises polystyrene and a plurality of europium atoms dispersed throughout the core.

10. A particle as in claim 1, wherein the outer layer comprises a polyarylene vinylene or a polyarylene ethynylene.

11. A particle as in claim 1, wherein B and D are each alkyne.

12. A particle as in claim 1, wherein the luminescent polymer comprises the structure,

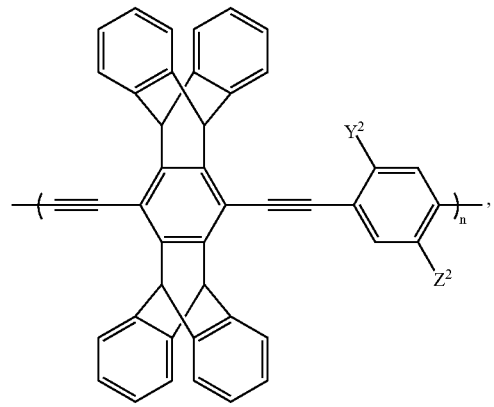

wherein $Y^2$ and $Z^2$ can be the same or different and are alkyl, heteroalkyl, or substituted derivatives thereof, or, $Y^2$ and $Z^2$ are joined together to form a ring.

13. A particle as in claim 12, wherein $Y^2$ and $Z^2$ are each ethylene glycol chains.

14. A particle as in claim 12, wherein $Y^2$ and $Z^2$ are each ethylene glycol chains substituted with a carboxylic acid group.

15. A particle as in claim 1, wherein the particle has a particle size between 0.001 and 10 microns.

16. A particle as in claim 1, wherein the particle has a particle size between 0.01 and 5.0 microns.

17. A particle as in claim 1, wherein the particle has a particle size between 0.01 and 3.0 microns.

18. A particle as in claim 1, wherein the particles has a particle size between 0.1 and 1.0 micron.

19. A particle as in claim 1, wherein the maximum of the first emission is separated from the maximum of the second emission by at least 100 nm.

20. A particle as in claim 1, wherein the maximum of the first emission is separated from the maximum of the second emission by at least 125 nm.

21. A particle as in claim 1, wherein the maximum of the first emission is separated from the maximum of the second emission by at least 150 nm.

22. A particle as in claim 1, further comprising a support material integrally connected to at least a portion of the particle such that the particle is substantially contained within the support material.

23. A particle as in claim 22, further comprising a quencher molecule attached to at least a portion of the support material via a linker such that the quencher molecule is not capable of interacting with the particle.

* * * * *

UNITED STATES PATENT AND TRADEMARK OFFICE
CERTIFICATE OF CORRECTION

PATENT NO. : 8,802,447 B2  
APPLICATION NO. : 11/595833  
DATED : August 12, 2014  
INVENTOR(S) : Timothy M. Swager et al.

Page 1 of 1

It is certified that error appears in the above-identified patent and that said Letters Patent is hereby corrected as shown below:

In the Specification

Please replace the paragraph beginning on column 1, line 8, with the following paragraph:

--This invention was made with Government support under Contract No. DAAD19-02-D-0002 awarded by the U.S. Army Research Office. The Government has certain rights in the invention.--

Signed and Sealed this  
Twenty-fifth Day of November, 2014

Michelle K. Lee  
*Deputy Director of the United States Patent and Trademark Office*